(12) United States Patent
Vuarier et al.

(10) Patent No.: US 7,402,180 B2
(45) Date of Patent: Jul. 22, 2008

(54) COMPOSITION FOR THE OXIDATION DYEING OF KERATIN FIBRES, COMPRISING AT LEAST ONE FATTY ALCOHOL CHOSEN FROM MONO- AND POLYGLYCEROLATED FATTY ALCOHOLS AND A PARTICULAR POLYOL

(75) Inventors: Patricia Vuarier, Levallois Perret (FR); Jean-Marie Millequant, Saint-Maur des Fosses (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 11/483,637

(22) Filed: Jul. 11, 2006

(65) Prior Publication Data

US 2006/0248664 A1 Nov. 9, 2006

Related U.S. Application Data

(63) Continuation of application No. 10/206,569, filed on Jul. 29, 2002, now abandoned.

(30) Foreign Application Priority Data

Jul. 27, 2001 (FR) .................................. 01 10116

(51) Int. Cl.
*A61Q 5/10* (2006.01)
(52) U.S. Cl. ...................... 8/405; 8/406; 8/408; 8/409; 8/410; 8/411; 8/421; 8/437; 8/492; 8/512; 8/519; 8/540; 8/554; 8/611
(58) Field of Classification Search ..................... 8/405, 8/406, 408, 409, 410, 411, 421, 437, 492, 8/512, 519, 540, 554, 611
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Dittmar | |
| 2,375,853 A | 5/1945 | Kirby et al. | |
| 2,388,614 A | 11/1945 | Kirby et al. | |
| 2,454,547 A | 11/1948 | Bock et al. | |
| 2,528,378 A | 10/1950 | Mannheimer | |
| 2,781,354 A | 2/1957 | Mannheimer | |
| 2,961,347 A | 11/1960 | Floyd | |
| 3,206,462 A | 9/1965 | McCarty | |
| 3,227,615 A | 1/1966 | Korden | |
| 3,632,559 A | 1/1972 | Matter et al. | |
| 3,836,537 A | 9/1974 | Boerwinkle et al. | |
| 3,874,537 A | 4/1975 | Green et al. | |
| 3,915,921 A | 10/1975 | Schlatzer, Jr. | |
| 3,917,817 A | 11/1975 | Vanterberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,003,699 A | 1/1977 | Rose et al. | |
| 4,005,193 A | 1/1977 | Green et al. | |
| 4,013,787 A | 3/1977 | Varlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,020 A | 5/1977 | Green et al. | |
| 4,031,307 A | 6/1977 | DeMartino et al. | |
| 4,131,576 A | 12/1978 | Iovine et al. | |
| 4,157,388 A | 6/1979 | Christiansen | |
| 4,172,887 A | 10/1979 | Vanlerberghe et al. | |
| 4,223,009 A | 9/1980 | Chakrabarti | |
| 4,277,581 A | 7/1981 | Vanlerberghe et al. | |
| 4,349,532 A | 9/1982 | Vanlerberghe et al. | |
| 4,445,521 A | 5/1984 | Grollier et al. | |
| 4,509,949 A | 4/1985 | Huang et al. | |
| 4,591,610 A | 5/1986 | Grollier | |
| 4,608,250 A | 8/1986 | Jacquet et al. | |
| 4,702,906 A | 10/1987 | Jacquet et al. | |
| 4,719,282 A | 1/1988 | Nadolsky et al. | |
| 4,761,273 A | 8/1988 | Grollier et al. | |

(Continued)

FOREIGN PATENT DOCUMENTS

DE          23 59 399          6/1975

(Continued)

OTHER PUBLICATIONS

English language Derwent Abstract of DE 197 55 491, May 12, 1999.

(Continued)

*Primary Examiner*—Eisa B Elhilo
(74) *Attorney, Agent, or Firm*—Finnegan, Henderson, Farabow, Garrett & Dunner, L.L.P.

(57) ABSTRACT

A composition for the oxidation dyeing of keratin fibers, such as human keratin fibers and further such as the hair, comprising, in a medium that is suitable for dyeing and that is free of glycerol and of cationic synthetic thickening polymer comprising at least one fatty chain, at least one oxidation dye, at least one fatty alcohol chosen from mono- and polyglycerolated fatty alcohols, and at least one particular polyol. The invention also relates to the dyeing processes and devices using the said composition.

54 Claims, No Drawings

U.S. PATENT DOCUMENTS

| | | | |
|---|---|---|---|
| 4,839,166 A | 6/1989 | Grollier et al. | |
| 5,061,289 A | 10/1991 | Clausen et al. | |
| 5,139,037 A | 8/1992 | Grollier et al. | |
| 5,196,189 A | 3/1993 | Jacquet et al. | |
| 5,376,146 A * | 12/1994 | Casperson et al. | 8/408 |
| 5,380,340 A | 1/1995 | Neunhoeffer et al. | |
| 5,518,506 A | 5/1996 | Cotteret et al. | |
| 5,710,311 A | 1/1998 | Junino et al. | |
| 5,735,908 A | 4/1998 | Cotteret et al. | |
| 5,766,576 A | 6/1998 | Lowe et al. | |
| 5,958,392 A * | 9/1999 | Grollier et al. | 424/70.17 |
| 5,984,975 A * | 11/1999 | Lagrange et al. | 8/412 |
| 6,099,592 A | 8/2000 | Vidal et al. | |
| 6,251,145 B1 | 6/2001 | De La Mettrie et al. | |
| 6,287,578 B1 | 9/2001 | Duetsch et al. | |
| 6,313,260 B2 | 11/2001 | Gruning et al. | |
| 2001/0023516 A1 | 9/2001 | Cottard et al. | |
| 2002/0004955 A1 | 1/2002 | Lang et al. | |
| 2002/0046431 A1 | 4/2002 | Laurent et al. | |

FOREIGN PATENT DOCUMENTS

| | | |
|---|---|---|
| DE | 38 43 892 | 6/1990 |
| DE | 41 33 957 | 4/1993 |
| DE | 195 43 988 | 5/1997 |
| DE | 197 55 491 | 5/1999 |
| EP | 0 080 976 | 6/1983 |
| EP | 0 122 324 | 10/1984 |
| EP | 0 173 109 | 3/1986 |
| EP | 0 216 479 | 4/1987 |
| EP | 0 337 354 | 10/1989 |
| EP | 0 767 191 | 4/1997 |
| EP | 0 884 344 | 12/1998 |
| EP | 0 943 320 | 9/1999 |
| EP | 0 959 090 | 11/1999 |
| EP | 0 959 091 | 11/1999 |
| EP | 0 959 094 | 11/1999 |
| EP | 0 962 220 | 12/1999 |
| EP | 1 179 336 | 2/2002 |
| FR | 1 400 366 | 4/1965 |
| FR | 1 492 597 | 7/1967 |
| FR | 1 583 363 | 10/1969 |
| FR | 2 077 143 | 9/1971 |
| FR | 2 080 759 | 11/1971 |
| FR | 2 162 025 | 7/1973 |
| FR | 2 190 406 | 1/1974 |
| FR | 2 252 840 | 6/1975 |
| FR | 2 280 361 | 2/1976 |
| FR | 2 270 846 | 12/1976 |
| FR | 2 316 271 | 1/1977 |
| FR | 2 320 330 | 3/1977 |
| FR | 2 336 434 | 7/1977 |
| FR | 2 368 508 | 5/1978 |
| FR | 2 393 573 | 1/1979 |
| FR | 2 413 907 | 8/1979 |
| FR | 2 383 660 | 10/1979 |
| FR | 2 470 596 | 8/1981 |
| FR | 2 505 348 | 11/1982 |
| FR | 2 519 863 | 7/1983 |
| FR | 2 542 997 | 9/1984 |
| FR | 2 598 611 | 11/1987 |
| FR | 2 733 749 | 11/1996 |
| FR | 2 803 195 | 7/2001 |
| GB | 1 026 978 | 4/1966 |
| GB | 1 153 198 | 5/1969 |
| JP | 2019576 | 1/1990 |
| JP | 9110659 | 4/1997 |
| WO | WO 94/08969 | 4/1994 |
| WO | WO 94/08970 | 4/1994 |
| WO | WO 96/15765 | 5/1996 |
| WO | WO 98/44012 | 10/1998 |

OTHER PUBLICATIONS

English language Derwent Abstract of EP 0 080 976, Jun. 8, 1983.
English language Derwent Abstract of EP 0 884 344, Dec. 16, 1998.
English language Derwent Abstract of EP 0 943 320, Sep. 22, 1999.
English language Derwent Abstract of EP 0959 091, Jun. 8, 1983.
English language Derwent Abstract of FR 2 077 143, Sep. 10, 1971.
English language Derwent Abstract of FR 2 080 759, Nov. 19, 1971.
English language Derwent Abstract of FR 2 320 330, Mar. 4, 1977.
English language Derwent Abstract of FR 2 336 434, Jul. 22, 1977.
English language Derwent Abstract of JP 2019576, Jan. 23, 1990.
G. Fonnum et al., "Associative thickeners. Part I: Synthesis rheology and aggregation behavior," Colloid & Polymer Science, vol. 271, No. 4, Apr. 1993, pp. 380-389.
M.R. Porter, "Handbook of Surfactants", Blackie & Son Ltd., Glasgow & London, 1991, pp. 117-178.

* cited by examiner

COMPOSITION FOR THE OXIDATION DYEING OF KERATIN FIBRES, COMPRISING AT LEAST ONE FATTY ALCOHOL CHOSEN FROM MONO- AND POLYGLYCEROLATED FATTY ALCOHOLS AND A PARTICULAR POLYOL

This is a continuation of application Ser. No. 10/206,569, filed Jun. 29, 2002, now abandoned, which claims the benefit of priority under 35 U.S.C. § 119 to French Patent Application No. 0110116, filed Jul. 27, 2001, the contents of which are incorporated herein by reference.

FIELD OF THE INVENTION

The present invention relates to a composition for the oxidation dyeing of keratin fibers, such as human keratin fibers and further such as the hair, comprising, in a medium that is suitable for dyeing and that is free of glycerol and of cationic synthetic thickening polymer comprising at least one fatty chain, at least one oxidation dye, at least one fatty alcohol chosen from mono- and polyglycerolated fatty alcohols and at least one particular polyol.

BACKGROUND OF THE INVENTION

It is known practice to dye keratin fibers, such as human hair, with dye compositions containing oxidation dye precursors, generally known as "oxidation bases." Representative "oxidation bases" are ortho- or para-phenylenediamines, ortho- or para-aminophenols and heterocyclic bases.

Oxidation dye precursors are compounds which are initially uncoloured or only weakly coloured and which develop their dyeing power on the hair in the presence of oxidizing agents leading to the formation of coloured compounds. The formation of these coloured compounds results either from an oxidative condensation of the "oxidation bases" with themselves or from an oxidative condensation of the "oxidation bases" with coloration modifiers, or "couplers", which are generally present in the dye compositions used in oxidation dyeing and are represented by meta-phenylenediamines, meta-aminophenols and meta-diphenols, and certain heterocyclic compounds.

The variety of molecules used, which comprise on the one hand the "oxidation bases" and on the other hand, the "couplers", allows a very wide range of colours to be obtained.

These oxidation bases and these couplers are formulated in vehicles that allow them to be applied to keratin fibers after mixing with an oxidizing agent.

These vehicles are generally aqueous and can comprise one or more surfactants, such as nonionic surfactants, that may be optionally combined with one or more solvents.

DETAILED DESCRIPTION OF THE INVENTION

However, the Inventors have found that the systems mentioned above are not always able to produce shades that are entirely satisfactory in terms of strength, chromaticity, or staying power. The Inventors have in particular found that at least certain dye compositions of the prior art cannot achieve a sufficient strength on sensitized hair.

After considerable research conducted in this matter, the Inventors have now discovered that it is possible to obtain oxidation dye compositions that can produce strong and chromatic (luminous) shades with good staying power with respect to chemical agents (shampoo, permanent-waving agents, etc.) or natural agents (light, perspiration, etc.), thus giving a satisfactory strength on sensitized hair, by introducing into the dye composition at least one fatty alcohol chosen from mono- and polyglycerolated fatty alcohols and at least one particular polyol.

These discoveries can be present, in full or in part, in embodiments of the present invention.

One subject of the present invention is thus a composition for the oxidation dyeing of keratin fibers, such as human keratin fibers and further such as the hair, comprising, in a medium that is suitable for dyeing, at least one oxidation dye, and characterized in that:

(a) said composition further comprises at least one fatty alcohol chosen from mono- and polyglycerolated fatty alcohols and at least one polyol of formula (Ia) below:

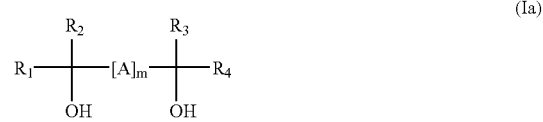

in which:
$R_1$, $R_2$, $R_3$, and $R_4$ are chosen from, independently of each other, a hydrogen atom, $C_1$-$C_6$ alkyl radicals, $C_1$-$C_6$ monohydroxyalkyl radicals, and $C_1$-$C_6$ polyhydroxyalkyl radicals;
A is chosen from linear and branched alkylene radicals containing a number of carbon atoms "n" ranging from 1 to 18, and optionally interrupted with a number of oxygen atoms "z" ranging from 0 to 9; and
m is chosen from 0 and 1;
wherein the total number of carbon atoms in both radical A and all of the substituents $R_1$, $R_2$, $R_3$, and $R_4$ is greater than or equal to 2;
wherein the molecular weight of said at least one polyol ranges (i) from 95 to 500, if m is equal to 0, or if m and n are equal to 1, or if m is equal to 1 and A is a linear alkylene radical and n is equal to 2 and z is equal to 0; or (ii) from 140 to 500, if n is greater than or equal to 2, or if m is equal to 1 and n is equal to 2 and z does not equal 0; or (iii) from 90 to 500, if m is equal to 1 and n does not equal 1 or 2 and z is equal to 0, or if m is equal to 1 and A is a branched alkylene radical and n is equal to 2 and z is equal to 0; and (b) said composition contains no glycerol and no cationic synthetic thickening polymer comprising at least one fatty chain.

Another subject of the invention relates to a ready-to-use composition for the oxidation dyeing of keratin fibers, which comprises, in a medium that is suitable for dyeing, at least one composition as described above and at least one oxidizing agent.

For the purposes of the present invention, the expression "ready-to-use composition" is defined herein as a composition to be applied immediately to the keratin fibers. Said "ready-to-use composition" may be stored in unmodified form before use, or may result from the extemporaneous mixing of two or more compositions.

The invention is also directed towards a process for the oxidation dyeing of keratin fibers, such as human keratin fibers such as the hair, comprising applying to the fibers a composition (A) comprising, in a medium that is suitable for dyeing, at least one oxidation dye in combination with at least one fatty alcohol chosen from mono- and polyglycerolated fatty alcohols and at least one polyol of formula (Ia) below:

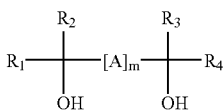

in which:

$R_1$, $R_2$, $R_3$, and $R_4$ are chosen from, independently of each other, a hydrogen atom, $C_1$-$C_6$ alkyl radicals, $C_1$-$C_6$ monohydroxyalkyl radicals, and $C_1$-$C_6$ polyhydroxyalkyl radicals;

A is chosen from linear and branched alkylene radicals containing a number of carbon atoms "n" ranging from 1 to 18, and optionally interrupted with a number of oxygen atoms "z" ranging from 0 to 9; and m is chosen from 0 and 1;

wherein the total number of carbon atoms in both radical A and all of the substituents $R_1$, $R_2$, $R_3$, and $R_4$ is greater than or equal to 2;

wherein the molecular weight of said at least one polyol ranges (i) from 95 to 500, if m is equal to 0, or if m and n are equal to 1, or if m is equal to 1 and A is a linear alkylene radical and n is equal to 2 and z is equal to 0; or (ii) from 140 to 500, if n is greater than or equal to 2, or if m is equal to 1 and n is equal to 2 and z does not equal 0; or (iii) from 90 to 500, if m is equal to 1 and n does not equal 1 or 2 and z is equal to 0, or if m is equal to 1 and A is a branched alkylene radical and n is equal to 2 and z is equal to 0; and containing no glycerol and no cationic synthetic thickening polymer comprising at least one fatty chain;

wherein the colour can be developed at alkaline, neutral, or acidic pH with the aid of a composition (B) comprising at least one oxidizing agent, which is mixed with composition (A) just at the time of use, or which is applied sequentially without intermediate rinsing.

A subject of the invention is also a multi-compartment dyeing device or "kit" for the oxidation dyeing of keratin fibers, such as human keratin fibers and further such as the hair, which comprises at least one first compartment comprising a composition, free of glycerol and free of cationic synthetic thickening polymer comprising at least one fatty chain, comprising at least one oxidation dye, at least one fatty alcohol chosen from mono- and polyglycerolated fatty alcohols and at least one polyol of formula (Ia) below:

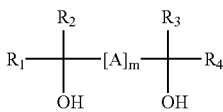

in which:

$R_1$, $R_2$, $R_3$, and $R_4$ are chosen from, independently of each other, a hydrogen atom, $C_1$-$C_6$ alkyl radicals, $C_1$-$C_6$ monohydroxyalkyl radicals, and $C_1$-$C_6$ polyhydroxyalkyl radicals; A is chosen from linear and branched alkylene radicals containing a number of carbon atoms "n" ranging from 1 to 18, and optionally interrupted with a number of oxygen atoms "z" ranging from 0 to 9; and m is chosen from 0 and 1;

wherein the total number of carbon atoms in both radical A and all of the substituents $R_1$, $R_2$, $R_3$, and $R_4$ is greater than or equal to 2;

wherein the molecular weight of said at least one polyol ranges (i) from 95 to 500, if m is equal to 0, or if m and n are equal to 1, or if m is equal to 1 and A is a linear alkylene radical and n is equal to 2 and z is equal to 0; or (ii) from 140 to 500, if n is greater than or equal to 2, or if m is equal to 1 and n is equal to 2 and z does not equal 0; or (iii) from 90 to 500, if m is equal to 1 and n does not equal 1 or 2 and z is equal to 0, or if m is equal to 1 and A is a branched alkylene radical and n is equal to 2 and z is equal to 0;, and a second compartment comprising at least one oxidizing agent.

However, other characteristics, aspects, objects, and advantages of certain embodiments of the invention should emerge even more clearly on reading the description and the examples that follow.

The expression "mono- and polyglycerolated fatty alcohols" is defined herein as any of the compounds corresponding to formula (IIa) below:

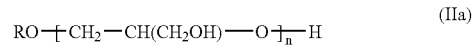

wherein R is chosen from saturated, and unsaturated, linear, and branched radicals comprising from 8 to 40 carbon atoms, such as from 10 to 30 carbon atoms;

and wherein n represents a number ranging from 1 to 30, such as from 1 to 10.

Compounds of this type that may be mentioned include, for example, lauryl alcohol containing 4 mol of glycerol (INCI name: polyglyceryl-4 lauryl ether), oleyl alcohol containing 4 mol of glycerol (INCI name: polyglyceryl-4 oleyl ether), oleyl alcohol containing 2 mol of glycerol (INCI name: polyglyceryl-2 oleyl ether), cetearyl alcohol containing 2 mol of glycerol, cetearyl alcohol containing 6 mol of glycerol, oleocetyl alcohol containing 6 mol of glycerol and octadecanol containing 6 mol of glycerol.

The fatty alcohol may represent a mixture of fatty alcohols in the same respect that the value of n represents a random value, which means that several species of polyglycerolated fatty alcohol may coexist in the form of a mixture in a commercial product.

The at least one fatty alcohol chosen from mono- and polyglycerolated fatty alcohols represents from about 0.01% to about 30%, such as from about 0.05% to about 20% and further such as from about 0.1% to about 15%, relative to the total weight of the composition.

Among the polyols of formula (Ia), and in which m=0, mention may be made of pinacol (2,3-dimethyl-2,3-butanediol) and 1,2,3-butanetriol.

Among the polyols of formula (Ia) that may be mentioned are those for which, in formula (Ia), m=1 and $R_1$ to $R_4$ are chosen, independently of each other, from a hydrogen atom and $C_1$-$C_6$ alkyl radicasI.

Additional polyols of formula (Ia) that may be mentioned are polyethylene glycols such as, for example, the product known as PEG-6 in the CTFA publication (International Cosmetic Ingredient Dictionary, Seventh Edition).

Polyols of formula (Ia) that can be used can, for example, be chosen from those in formula (Ia) for which m=1, $R_1$ to $R_4$ are chosen, independently of each other, from a hydrogen atom and $C_1$-$C_6$ alkyl radicals, and which have a molecular weight of less than 200.

Representative polyols of this type can be chosen from 3-methyl-1,3,5-pentanetriol, 1,2,4-butanetriol, 1,5-pentanediol, 2-methyl-1,3-propanediol, 3-methyl-1,5-pentanediol, neopentyl glycol, also called 2,2-dimethyl-1,3-propanediol, isoprene glycol, also called 3-methyl-1,3-butanediol, and hexylene glycol, also called 2-methyl-2,4-pentanediol. Additional representative polyols of this type include hexylene glycol, neopentyl glycol, and 3-methyl-1,5-pentanediol.

The at least one polyols of formula (Ia) represents from about 0.1% to about 40%, such as from about 0.5% to about 30% and further such as from about 1% to about 20% relative to the total weight of the composition.

The oxidation dyes that may be used according to the invention can be chosen from oxidation bases and/or couplers.

In one embodiment of the invention, the compositions comprise at least one oxidation base.

The oxidation bases that may be used in the context of the present invention can be chosen from those conventionally known in oxidation dyeing, such as ortho- and para-phenylenediamines, double bases, ortho- and para-aminophenols, heterocyclic bases such as those described below, and also the addition salts thereof with an acid.

An example of a hetercyclic base which may be used is the para-phenylenediamines of formula (II) below, and the addition salts thereof with an acid:

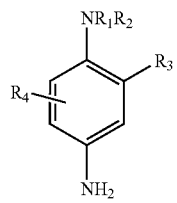

(II)

wherein
$R_1$ is chosen from a hydrogen atom, $C_1$-$C_4$ alkyl radicals, $C_1$-$C_4$ monohydroxyalkyl radicals, $C_2$-$C_4$ polyhydroxyalkyl radicals, ($C_1$-$C_4$)alkoxy($C_1$-$C_4$)alkyl radicals and $C_1$-$C_4$ alkyl radicals substituted with a group chosen from nitrogenous, phenyl, and 4'-aminophenyl groups;
$R_2$ is chosen from a hydrogen atom, $C_1$-$C_4$ alkyl radicals, $C_1$-$C_4$ monohydroxyalkyl radicals, $C_2$-$C_4$ polyhydroxyalkyl radicals, ($C_1$-$C_4$)alkoxy($C_1$-$C_4$)alkyl radicals and $C_1$-$C_4$ alkyl radicals substituted with a nitrogenous group;
$R_1$ and $R_2$ optionally form, with the nitrogen atom which bears them, a heterocycle chosen from 5- and 6-membered nitrogenous heterocycles optionally substituted with at least one substituent chosen from alkyl, hydroxyl, and ureido groups;
$R_3$ is chosen from a hydrogen atom, a halogen atom, such as a chlorine atom, $C_1$-$C_4$ alkyl radicals, a sulpho radical, a carboxy radical, $C_1$-$C_4$ monohydroxyalkyl radicals, $C_1$-$C_4$ hydroxyalkoxy radicals, acetylamino($C_1$-$C_4$)alkoxy radicals, mesylamino($C_1$-$C_4$)alkoxy radicals, and carbamoylamino($C_1$-$C_4$)alkoxy radicals; and
$R_4$ is chosen from a hydrogen atom, a halogen atom, and $C_1$-$C_4$ alkyl radicals.

Among the nitrogenous groups of formula (II) above, mention may be made of, for example, amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium, and ammonium radicals.

Among the para-phenylenediamines of formula (II) above, further mention may be made, for example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(,3-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxy-ethyloxy-para-phenylenediamine, 2-β-acetylaminoethyloxy-para-phenylenediamine, N-(β-methoxyethyl)-para-phenylenediamine, and 2-methyl-1-N-β-hydroxyethyl-para-phenylenediamine, and the addition salts thereof with an acid.

Among the para-phenylenediamines of formula (II) above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, and 2-chloro-para-phenylenediamine, and the addition salts thereof with an acid.

As disclosed herein, the term double bases is defined as compounds comprising at least two aromatic nuclei bearing amino and/or hydroxyl groups.

In an embodiment of the invention, double bases which can be used as oxidation bases in the dye compositions include, for example, compounds corresponding to formula (III) below, and the addition salts thereof with an acid:

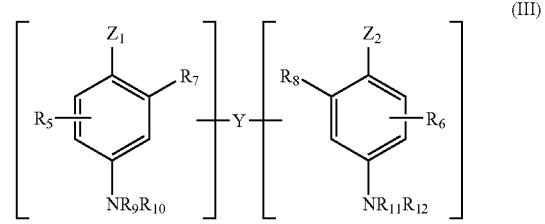

(III)

wherein:
$Z_1$ and $Z_2$, which may be identical or different, are chosen from a hydroxyl radical and a —$NH_2$ radical which may be substituted with at least one substituent chosen from $C_1$-$C_4$ alkyl radicals and a linker arm Y;
the linker arm Y is chosen from linear and branched alkylene chains comprising from 1 to 14 carbon atoms, which may be interrupted by or terminated with at least one entity chosen from nitrogenous groups and hetero atoms, such as oxygen, sulphur, and nitrogen atoms, and optionally substituted with at least one radical chosen from hydroxyl and $C_1$-$C_6$ alkoxy radicals;
$R_5$ and $R_6$ are chosen from a hydrogen atom, a halogen atom, $C_1$-$C_4$ alkyl radicals, $C_1$-$C_4$ monohydroxyalkyl radicals, $C_2$-$C_4$ polyhydroxyalkyl radicals, $C_1$-$C_4$ aminoalkyl radicals, and a linker arm Y;

$R_7$, $R_8$, $R_9$, $R_{10}$, $R_{11}$ and $R_{12}$, which may be identical or different, are chosen from a hydrogen atom, a linker arm Y, and $C_1$-$C_4$ alkyl radicals;

wherein the compounds of formula (III) comprise only one linker arm Y per molecule.

Among the nitrogenous groups of formula (III) above, mention may be made of amino, mono($C_1$-$C_4$)alkylamino, di($C_1$-$C_4$)alkylamino, tri($C_1$-$C_4$)alkylamino, monohydroxy ($C_1$-$C_4$)alkylamino, imidazolinium, and ammonium radicals.

Among the double bases of formula (III) above, mention may be made of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)-tetramethylenediamine, N,N'-bis(4-methylaminophenyl) tetramethylenediamine, N,N'-bis-(ethyl)-N,N'-bis(4'-amino-3'-methylphenyl)ethylenediamine, and 1,8-bis(2,5-diaminophenoxy)-3,5-dioxaoctane, and the addition salts thereof with an acid.

Additional representative double bases of formula (III) include, for example, N,N'-bis(β-hydroxyethyl)-N,N'-bis(4'-aminophenyl)-1,3-diaminopropanol, and 1,8-bis(2,5-diaminophenoxy)-3,5-dioxaoctane, and one of the addition salts thereof with an acid. Representative para-aminophenols which can be used, for example, include those para-aminophenols corresponding to formula (IV) below, and the addition salts thereof with an acid:

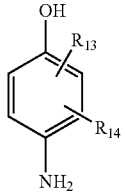

(IV)

wherein:

$R_{13}$ is chosen from a hydrogen atom, a halogen atom such as fluorine, and $C_1$-$C_4$ alkyl, $C_1$-$C_4$ monohydroxyalkyl, ($C_1$-$C_4$)alkoxy($C_1$-$C_4$)alkyl, $C_1$-$C_4$ aminoalkyl, and hydroxy($C_1$-$C_4$)alkylamino($C_1$-$C_4$)alkyl radicals;

$R_{14}$ is chosen from a hydrogen atom, a halogen atom such as fluorine, and $C_1$-$C_4$ alkyl, $C_1$-$C_4$ monohydroxyalkyl, $C_2$-$C_4$ polyhydroxyalkyl, $C_1$-$C_4$ aminoalkyl, $C_1$-$C_4$ cyanoalkyl, and ($C_1$-$C_4$)alkoxy($C_1$-$C_4$)alkyl radicals.

Among the para-aminophenols of formula (IV) above, mention may be made, for example, of para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, and 4-amino-2-(β-hydroxyethylaminomethyl)phenol, and the addition salts thereof with an acid.

Representative ortho-aminophenols which can be used as oxidation bases in the context of the present invention include, for instance, 2-aminophenol, 2-amino-1-hydroxy-5-methylbenzene, 2-amino-1-hydroxy-6-methylbenzene, and 5-acetamido-2-aminophenol, and the addition salts thereof with an acid.

Representative heterocyclic bases which can be used as oxidation bases in the dye compositions in accordance with the invention include, for instance, pyridine derivatives, pyrimidine derivatives, and pyrazole derivatives, and the addition salts thereof with an acid.

Such pyridine derivatives may include the compounds described, for example, in patents GB 1 026 978 and GB 1 153 196 (the disclosures of which are incorporated herein by reference), such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, and 3,4-diaminopyridine, and the addition salts thereof with an acid.

Additional pyrimidine derivatives which may be used include those compounds described, for example, in German patent DE 2 359 399 or Japanese patents JP 88-169 571 and JP 91-10659 or patent application WO 96/15765 (the disclosures of which are incorporated herein by reference), such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, and 2,5,6-triaminopyrimidine, and pyrazolopyrimidine derivatives such as those mentioned in patent application FR-A-2 750 048 (the disclosure of which is incorporated herein by reference) and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-aminopyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof and the tautomeric forms thereof, when a tautomeric equilibrium exists, and the addition salts thereof with an acid.

Among the pyrazole derivatives, mention may also be made of the compounds described in patents DE 3 843 892, DE 4 133 957 and patent applications WO 94/08969, WO 94/08970, FR-A-2 733 749 and DE 195 43 988 (the disclosures of which are incorporated herein by reference), such as 4,5-diamino-1-methylpyrazole, 3,4-diaminopyrazole, 4,5-diamino-1-(4'-chlorobenzyl)pyrazole, 4,5-diamino-1,3-dimethyl-pyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methyl pyrazole, 4,5-diamino-1-tert-butyl-3-methyl pyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropyl-pyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the addition salts thereof with an acid.

In an embodiment of the invention, the oxidation bases represent from 0.0005% to 12% by weight approximately relative to the total weight of the composition, such as from 0.005% to 8% by weight approximately relative to this weight.

The couplers which may be used in the dye composition according to the invention include those conventionally used in oxidation dye compositions, such as meta-aminophenols, meta-phenylenediamines, meta-diphenols, naphthols, and heterocyclic couplers such as indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the addition salts thereof with an acid.

Representative couplers that can be used include 2,4-diamino-1-(β-hydroxyethyloxy)benzene, 2-methyl-5-aminophenol, 5-N-(β-hydroxyethyl )amino-2-methylphenol, 3-aminophenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methyl pyrazol-5-one, 2-amino-3-hydroxypyridine, 3,6-dimethylpyrazolo[3,2-c]-1,2,4-triazole, and 2,6-dimethylpyrazolo[1,5-b]-1,2,4-triazole, and the addition salts thereof with an acid.

When they are present, these couplers represent from 0.0001% to 10% by weight approximately relative to the total weight of the composition, such as from 0.005% to 5% by weight approximately.

In general, the addition salts with an acid of the oxidation bases and couplers can be hydrochlorides, hydrobromides, sulphates, tartrates, lactates, and/or acetates.

In addition to the oxidation dyes mentioned above, the composition according to the invention may also comprise direct dyes to enrich the shades with glints. In this case, these direct dyes may be chosen from neutral, cationic, anionic, nitro, azo, or anthraquinone dyes, in a weight proportion from about 0.001% to 20% relative to the total weight of the composition, such as from 0.01% to 10% relative to the total weight of the composition.

In an embodiment of the invention, a ready-to-use composition which can be used according to the invention include composition (A) and/or composition (B) that may also comprise at least one cationic or amphoteric polymer.

Cationic Polymers

For the purposes of the present invention as disclosed herein, the expression "cationic polymer" is defined as any polymer comprising cationic groups and/or groups which may be ionized into cationic groups.

Representative cationic polymers which may be used in accordance with the present invention may be chosen from any of those already known in the art for improving the cosmetic properties of the hair, such as those described, for example, in patent application EP-A-337 354 and in French patents FR-2 270 846, 2 383 660, 2 598 611, 2 470 596 and 2 519 863 (the disclosures of which are incorporated herein by reference).

Cationic polymers which may be used include those cationic polymer comprising units which comprise of primary, secondary, tertiary, and/or quaternary amine groups, which may either form part of the main polymer chain or may be borne by a side substituent directly attached thereto.

Said cationic polymers can have an approximate number-average molecular mass of from about 500 to about $5 \times 10^6$ such as from about $10^3$ to about $3 \times 10^6$.

Additional cationic polymers which may be mentioned are polymers of the polyamine, polyamino amide, and polyquaternary ammonium type.

Said cationic polymers are products that are well known to one of ordinary skill in the art. They are described, for example, in French patents 2 505 348 and 2 542 997 (the disclosures of which are incorporated herein by reference). Among said polymers, mention may be made, for instance, of:

(1) homopolymers or copolymers derived from acrylic esters, methacrylic esters, or amides and comprising at least one of the units of formula (V), (VI), (VII), or (VIII) below:

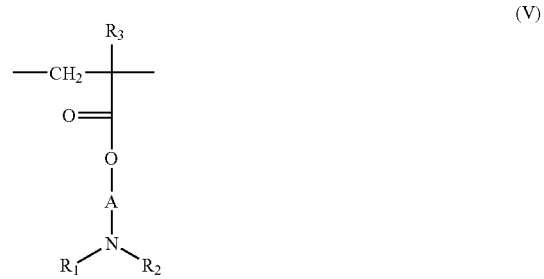

(V)

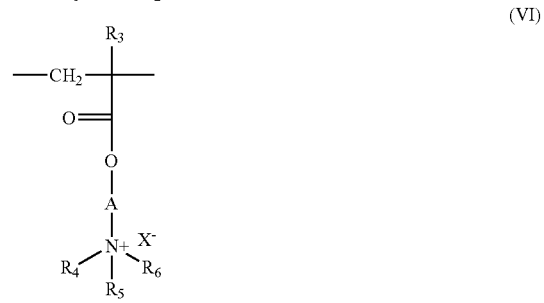

(VI)

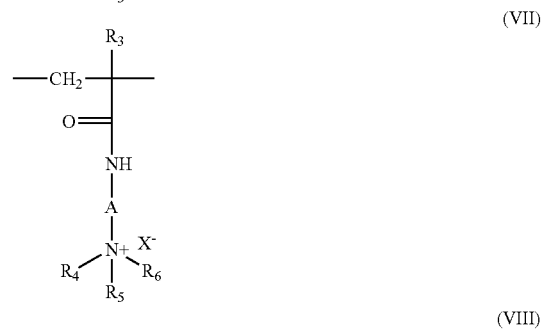

(VII)

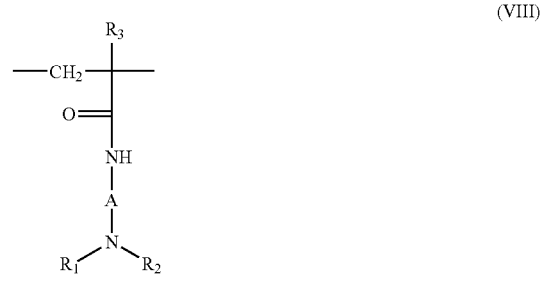

(VIII)

wherein $R_3$, which may be identical or different, denote a hydrogen atom or a $CH_3$ radical;

A, which may be identical or different, represent a linear or branched alkyl group of 1 to 6 carbon atoms such as 2 or 3 carbon atoms, or a hydroxyalkyl group of 1 to 4 carbon atoms;

$R_4$, $R_5$ and $R_6$, which may be identical or different, represent an alkyl group comprising 1 to 18 carbon atoms such as an alkyl group comprising from 1 to 6 carbon atoms, or a benzyl radical;

$R_1$ and $R_2$, which may be identical or different, represent hydrogen or an alkyl group comprising from 1 to 6 carbon atoms, such as methyl or ethyl;

X denotes an anion derived from an inorganic or organic acid, such as a methosulphate anion or a halide such as chloride or bromide.

The homopolymers or copolymers of (1) can further comprise one or more units derived from comonomers which may be chosen from acrylamides, methacrylamides, diacetone-acrylamides, acrylamides, methacrylamides substituted on the nitrogen with lower ($C_1$-$C_4$)alkyls, acrylic, or methacrylic acids or esters thereof, vinyllactams such as vinylpyrrolidone or vinylcaprolactam, and vinyl esters.

Thus, among homopolymers or copolymers of (1), mention may be made, for example, of:

copolymers of acrylamide and of dimethylaminoethyl methacrylate quaternized with dimethyl sulphate or with a dimethyl halide, such as the product sold under the name Hercofloc by the company Hercules, the copolymers of acrylamide and of methacryloyloxyethyltrimethylammonium chloride described, for example, in patent application EP-A-080 976 and sold under the name Bina Quat P 100 by the company Ciba Geigy, the copolymer of acrylamide and of methacryloyloxyethyltrimethylammonium methosulphate sold under the name Reten by the company Hercules, quaternized or non-quaternized vinyipyrrolidoneidialkylaminoalkyl acrylate or methacrylate copolymers, such as the products sold under the name "Gafquat" by the company ISP, such as, for example, "Gafquat 734" or "Gafquat 755", or alternatively the products known as "Copolymer 845, 958 and 937". These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, and quaternized vinylpyrrolidone/dimethylaminopropylmethacrylamide copolymers such as the product sold under the name "Gafquat HS 100" by the company ISP.

(2) The cellulose ether derivatives containing quaternary ammonium groups, described in French patent 1 492 597 (the disclosure of which is incorporated herein by reference), such as polymers sold under the names "JR" (JR 400, JR 125 and JR 30M) or "LR" (LR 400, or LR 30M) by the company Union Carbide Corporation. These polymers are also defined in the CTFA dictionary as quaternary ammoniums of hydroxyethylcellulose which has reacted with an epoxide substituted with a trimethylammonium group.

(3) Cationic cellulose derivatives such as cellulose copolymers or cellulose derivatives grafted with a water-soluble monomer of quaternary ammonium, and described for example in U.S. Pat. No. 4,131,576 (the disclosure of which is incorporated herein by reference), such as hydroxyalkylcelluloses, for instance hydroxymethyl-, hydroxyethyl-, or hydroxypropylcelluloses grafted with a methacryloyloxyethyltrimethylammonium, methacrylamidopropyltrimethylammonium, or dimethyldiallylammonium salt, for instance.

The commercial products corresponding to this definition, for instance, are sold under the names "Celquat L 200" and "Celquat H 100" by the company National Starch.

(4) The cationic polysaccharides described, for example, in U.S. Pat. Nos. 3,589,578 and 4,031,307 (the disclosures of which are incorporated herein by reference), such as guar gums comprising cationic trialkylammonium groups. Guar gums modified with a salt (e.g. chloride) of 2,3-epoxypropyltrimethylammonium can be used, for example.

Such products are sold, for instance, under the trade names Jaguar C13 S, Jaguar C 15, Jaguar C 17, or Jaguar C162 by the company Meyhall.

(5) Polymers comprising of piperazinyl units and of divalent alkylene or hydroxyalkylene radicals comprising straight or branched chains, optionally interrupted by oxygen, sulphur, or nitrogen atoms or by aromatic or heterocyclic rings, and also the oxidation and/or quaternization products of these polymers. Such polymers are described, for example, in French patents 2 162 025 and 2 280 361 (the disclosures of which are incorporated herein by reference).

(6) Water-soluble polyamino amides prepared, for example, by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide, or alternatively with an oligomer resulting from the reaction of a difunctional compound which is reactive with a bis-halohydrin, a bis-azetidinium, a bis-haloacyidiamine, a bis-alkyl halide, an epihalohydrin, a diepoxide, or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, for example, in French patents 2 252 840 and 2 368 508 (the disclosures of which are incorporated herein by reference).

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers in which the alkyl radical comprises from 1 to 4 carbon atoms and preferably denotes methyl, ethyl, or propyl. Such polymers are described for example in French patent 1 583 363 (the disclosure of which is incorporated herein by reference).

Among these derivatives, further mention may be made of the adipic acid/dimethylaminohydroxypropyl/diethylenetriamine polymers sold under the name "Cartaretine F, F4 or F8" by the company Sandoz, for example.

(8) The polymers obtained by reaction of a polyalkylene polyamine comprising two primary amine groups and at least one secondary amine group with a dicarboxylic acid chosen from diglycolic acid and saturated aliphatic dicarboxylic acids comprising from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described, for example, in U.S. Pat. Nos. 3,227,615 and 2,961,347 (the disclosures of which are incorporated herein by reference).

Polymers of this type are sold under the name "Hercosett 57" by the company Hercules Inc. or alternatively under the name "PD 170" or "Delsette 101" by the company Hercules, for example, in the case of the adipic acid/epoxypropyl/diethylenetriamine copolymer.

(9) Cyclopolymers of alkyldiallylamine or of dialkyldiallylammonium, such as the homopolymers or copolymers comprising, as main constituent of the chain, units corresponding to formula (IX) or (X):

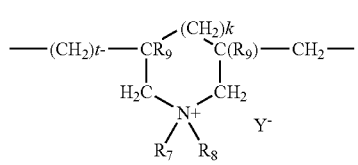

(IX)

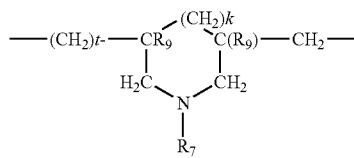

(X)

in which formulae k and t are equal to 0 or 1, the sum k+t being equal to 1; $R_9$ denotes a hydrogen atom or a methyl radical; $R_7$ and $R_8$, independently of each other, denote an alkyl group comprising from 1 to 6 carbon atoms, a hydroxyalkyl group in which the alkyl group comprises 1 to 5 carbon atoms, a lower $C_1$-$C_4$ amidoalkyl group, or $R_7$ and $R_8$ can denote, together with the nitrogen atom to which they are attached, heterocyclic groups such as piperidyl or morpholinyl; $R_7$ and $R_8$, independently of each other, denote an alkyl group comprising from 1 to 4 carbon atoms; $Y^-$ is an anion such as bromide, chloride, acetate, borate, citrate, tartrate, bisulphate, bisulphite, sulphate, or phosphate. These polymers are described, for example, in French patent 2 080 759 and in its Certificate of Addition 2 190 406 (the disclosures of which are incorporated herein by reference).

Among the polymers defined above, mention may be made, for example, of the dimethyldiallylammonium chloride homopolymer sold under the name "Merquat 100" by the company Calgon (and its homologues of low weight-average molecular mass) and copolymers of diallyldimethylammonium chloride and of acrylamide, sold under the name "Merquat 550".

(10) The quaternary diammonium polymer comprising repeating units corresponding to the formula:

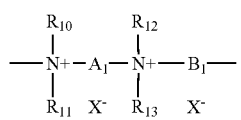

(XI)

wherein:

$R_{10}$, $R_{11}$, $R_{12}$ and $R_{13}$, which may be identical or different, represent aliphatic, alicyclic, or arylaliphatic radicals comprising from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally comprising a second hetero atom other than nitrogen, or alternatively $R_{10}$, $R_{11}$, $R_{12}$ and $R_{13}$ represent a linear or branched $C_1$-$C_6$ alkyl radical substituted with a nitrile, ester, acyl, or amide group or a group —CO—O—$R_{14}$-D or —CO—NH—$R_{14}$-D where $R_{14}$ is an alkylene and D is a quaternary ammonium group;

$A_1$ and $B_1$ represent polymethylene groups comprising from 2 to 20 carbon atoms which may be linear or branched, saturated or unsaturated, and which may comprise, linked to or intercalated in the main chain, one or more aromatic rings or one or more oxygen or sulphur atoms or sulphoxide, sulphone, disulphide, amino, alkylamino, hydroxyl, quaternary ammonium, ureido, amide, or ester groups, and $X^-$ denotes an anion derived from a mineral or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO-D-OC—$(CH_2)_n$— in which D denotes:

a) a glycol residue of formula: —O—Z—O—, where Z denotes a linear or branched hydrocarbon-based radical or a group corresponding to one of the following formulae:

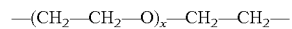

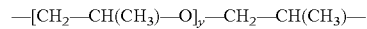

where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the divalent radical

d) a ureylene group of formula: —NH—CO—NH—.

Substituent $X^-$ can be an anion such as chloride or bromide, for example.

These polymers can have a number-average molecular mass of from 1,000 to 100,000.

Polymers of this type are described, for example, in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020 (the disclosures of which are incorporated herein by reference).

It is also possible to use polymers which comprise repeating units corresponding to formula (XII) below:

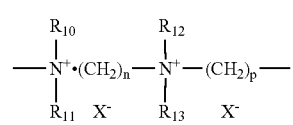

(XII)

in which $R_{10}$, $R_{11}$, $R_{12}$ and $R_{13}$, which may be identical or different, denote an alkyl or hydroxyalkyl radical comprising from 1 to 4 carbon atoms approximately, n and p are integers ranging from 2 to 20 approximately, and $X^-$ is an anion derived from a mineral or organic acid.

(11) Polyquaternary ammonium polymers comprising of repeating units of formula (XIII):

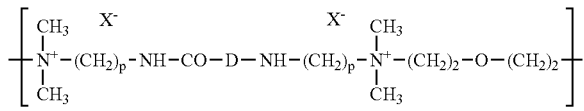
(XIII)

in which p denotes an integer ranging from 1 to 6 approximately, D may be nothing or may represent a group —$(CH_2)_r$—CO— in which r denotes a number equal to 4 or 7, $X^-$ is an anion.

Such polymers may be prepared according to the processes described, for example, in U.S. Pat. Nos. 4,157,388, 4,702,906, and 4,719,282 (the disclosures of which are incorporated herein by reference). They are also described, for example, in patent application EP-A-122 324 (the disclosure of which is incorporated herein by reference).

Among these products, mention may be made, for example, of "Mirapol A 15", "Mirapol AD1", "Mirapol AZ1" and "Mirapol 175" sold by the company Miranol.

(12) Quaternary polymers of vinylpyrrolidone and of vinylimidazole, such as, for example, the products sold under the names Luviquat FC 905, FC 550 and FC 370 by the company BASF.

(13) Polyamines such as Polyquart H sold by Henkel, which are given under the reference name "Polyethylene glycol (15) tallow polyamine" in the CTFA dictionary.

(14) Crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound comprising olefinic unsaturation, such as methylenebisacrylamide. A crosslinked acrylamide/methacryloyloxyethyltrimethylammonium chloride copolymer (20/80 by weight) in the form of a dispersion containing 50% by weight of the said copolymer in mineral oil can also be used, for example. This dispersion is sold under the name "Salcare® SC 92" by the company Allied Colloids. A crosslinked methacryloyloxyethyltrimethylammonium chloride homopolymer comprising about 50% by weight of the homopolymer in mineral oil or in a liquid ester can also be used. These dispersions, for example, are sold under the names "Salcare® SC 95" and "Salcare® SC 96" by the company Allied Colloids.

Other cationic polymers which can be used in the context of the invention are polyalkyleneimines, polymers comprising vinylpyridine or vinylpyridinium units, condensates of polyamines and of epichlorohydrin, quaternary polyureylenes and chitin derivatives.

Other representative cationic polymers which may be used in the context of the present invention include polymers of (1), (9), (10), (11), (14), and additional polymers comprising of repeating units of formulae (W) and (U) below:

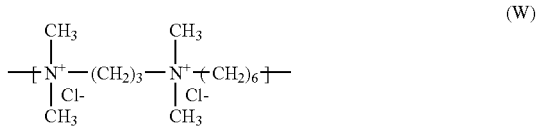
(W)

wherein the weight-average molar mass, determined by gel permeation chromatography, ranges from 9,500 to 9,900;

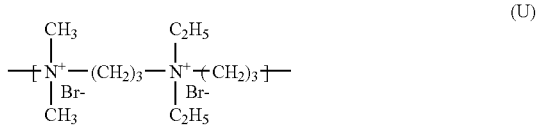
(U)

wherein the weight-average molar mass, determined by gel permeation chromatography, is about 1200.

The concentration of cationic polymer in the composition according to the present invention may range from 0.01% to 10% by weight relative to the total weight of the composition, such as from 0.05% to 5% and further such as from 0.1% to 3%.

Amphoteric Polymers

The amphoteric polymers which may be used in accordance with the present invention may be chosen from polymers comprising units K and M randomly distributed in the polymer chain, in which K denotes a unit derived from a monomer comprising at least one basic nitrogen atom and M denotes a unit derived from an acidic monomer comprising one or more carboxylic or sulphonic groups, or alternatively K and M may denote groups derived from zwitterionic carboxybetaine or sulphobetaine monomers;

K and M may also denote a cationic polymer chain comprising primary, secondary, tertiary, or quaternary amine groups, in which at least one of the amine groups bears a carboxylic or sulphonic group linked via a hydrocarbon-based radical, or alternatively K and M forms part of a chain of a polymer containing an α,β-dicarboxylic ethylene unit in which one of the carboxylic groups has been made to react with a polyamine comprising one or more primary or secondary amine groups.

The amphoteric polymers corresponding to the above definition can be chosen from the following polymers:

(1) polymers resulting from the copolymerization of a monomer derived from a vinyl compound bearing a carboxylic group, such as acrylic acid, methacrylic acid, maleic acid, α-chloroacrylic acid, and a basic monomer derived from a substituted vinyl compound comprising at least one basic atom, such as dialkylaminoalkyl methacrylate and acrylate, dialkylaminoalkylmethacrylamide and -acrylamide. Such compounds are described, for example, in U.S. Pat. No. 3,836,537 (the disclosure of which is incorporated herein by reference).

Mention may also be made of the sodium acrylate/acrylamidopropyltrimethylammonium chloride copolymer sold under the name Polyquart KE 3033 by the company Henkel.

The vinyl compound may also be a dialkyldiallylammonium salt such as dimethyldiallylammonium chloride. The copolymers of acrylic acid and of the latter monomer are sold under the names Merquat 280, Merquat 295 and Merquat Plus 3330 by the company Calgon.

(2) polymers comprising units derived from:
a) at least one monomer chosen from acrylamides and methacrylamides substituted on the nitrogen with an alkyl radical,
b) at least one acidic comonomer comprising one or more reactive carboxylic groups, and
c) at least one basic comonomer such as esters comprising primary, secondary, tertiary, and/or quaternary amine substituents of acrylic and methacrylic acids and the product of quaternization of dimethylaminoethyl methacrylate with dimethyl or diethyl sulphate.

The N-substituted acrylamides or methacrylamides which can be used according to the invention are groups wherein the alkyl radicals comprise from 2 to 12 carbon atoms such as N-ethylacrylamide, N-tert-butylacrylamide, N-tert-octylacrylamide, N-octylacrylamide, N-decylacrylamide, N-dodecylacrylamide, and the corresponding methacrylamides.

The acidic comonomers can be chosen from acrylic acid, methacrylic acid, crotonic acid, itaconic acid, maleic acid, fumaric acid, and alkyl monoesters, comprising 1 to 4 carbon atoms, of maleic or fumaric acids or anhydrides.

Representative basic comonomers are aminoethyl, butylaminoethyl, N,N'-dimethylaminoethyl, and N-tert-butylaminoethyl methacrylates.

The copolymers whose CTFA (4th edition, 1991) name is octylacrylamide/acrylates/butylaminoethyl methacrylate copolymer such as the products sold under the name Amphomer or Lovocryl 47 by the company National Starch can be used.

(3) crosslinked and alkylated polyamino amides partially or totally derived from polyamino amides of general formula:

in which $R_{19}$ represents a divalent radical derived from a saturated dicarboxylic acid, a mono- or dicarboxylic aliphatic acid containing an ethylenic double bond, an ester of a lower alkanol, comprising 1 to 6 carbon atoms, of these acids or a radical derived from the addition of any one of the said acids to a bis(primary) or bis(secondary) amine, and Z denotes a bis(primary), mono- or bis(secondary) polyalkylenepolyamine radical and represents:
a) in proportions of from 60 to 100 mol %, the radical

where x=2 and p=2 or 3, or alternatively x=3 and p=2;

this radical being derived from diethylenetriamine, from triethylenetetraamine, or from dipropylenetriamine;
b) in proportions of from 0 to 40 mol %, the radical (XV) above in which x=2 and p=1 and which is derived from ethylenediamine, or the radical derived from piperazine:

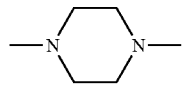

c) in proportions of from 0 to 20 mol %, the —NH—$(CH_2)_6$—NH— radical derived from hexamethylenediamine, these polyamino amines being crosslinked by addition of a difunctional crosslinking agent chosen from epihalohydrins, diepoxides, dianhydrides, and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids can be chosen from acids comprising 6 to 10 carbon atoms, such as adipic acid, 2,2,4-trimethyladipic acid, 2,4,4-trimethyladipic acid, terephthalic acid, and acids containing an ethylenic double bond such as, for example, acrylic acid, methacrylic acid, and itaconic acid.

The alkane sultones used in the alkylation can be propane sultone or butane sultone, and the salts of the alkylating agents can be the sodium or potassium salts.
(4) polymers containing zwitterionic units of formula:

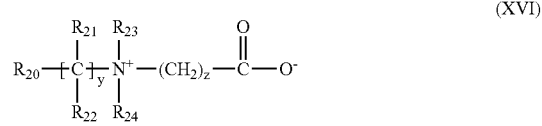

wherein $R_{20}$ denotes a polymerizable unsaturated group such as an acrylate, methacrylate, acrylamide, or methacrylamide group, y and z represent an integer from 1 to 3, $R_{21}$ and $R_{22}$ represent a hydrogen atom, methyl, ethyl or propyl, $R_{23}$ and $R_{24}$ represent a hydrogen atom or an alkylradical such that the sum of the carbon atoms in $R_{23}$ and $R_{24}$ does not exceed 10.

The polymers comprising such units can also comprise units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of methyl methacrylate/methyl dimethylcarboxymethylammonioethylmethacrylate such as the product cold under the mane Diaformer Z301 by the company Sandoz.
(5) polymers derived from chitosan containing monomer units corresponding to formulae (XVII), (XVIII) and (XIX) below:

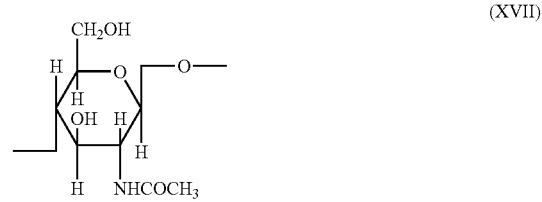

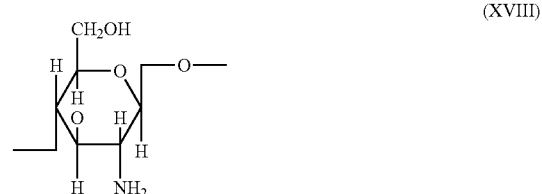

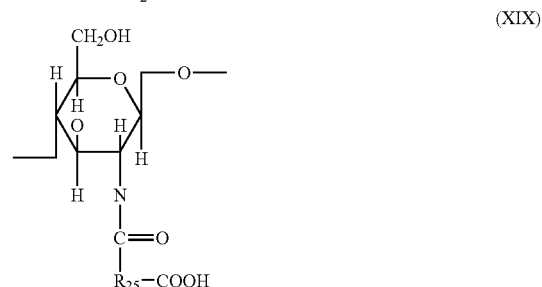

the unit (XVII) being present in proportions of between 0 and 30%, the unit (XVIII) in proportions of between 5% and 50% and the unit (XIX) in proportions of between 30% and 90%, it being understood that, in this unit (XIX), $R_{25}$ represents a radical of formula:

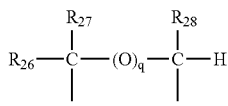

in which q denotes zero or 1;

if q=0, $R_{26}$, $R_{27}$ and $R_{28}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulphonic groups, an alkylthio residue in which the alkyl group bears an amino residue, at least one of the radicals $R_{26}$, $R_{27}$ and $R_{28}$ being, in this case, a hydrogen atom;

or, if q=1, $R_{26}$, $R_{27}$ and $R_{28}$ each represent a hydrogen atom, and also the salts formed by these compounds with bases or acids.

(6) polymers derived from the N-carboxyalkylation of chitosan, such as N-carboxymethylchitosan or N-carboxybutylchitosan sold under the name "Evalsan" by the company Han Dekker.

(7) polymers corresponding to the general formula (XX) as described, for example, in French patent 1 400 366 (the disclosure of which is incorporated herein by reference):

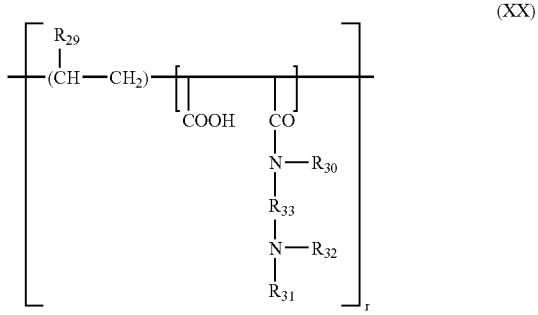

in which $R_{29}$ represents a hydrogen atom, a $CH_3O$, $CH_3CH_2O$ or phenyl radical, $R_{30}$ denotes hydrogen or a lower alkyl radical such as methyl or ethyl, $R_{31}$ denotes hydrogen or a lower alkyl radical such as methyl or ethyl, $R_{32}$ denotes a lower alkyl radical such as methyl or ethyl or a radical corresponding to the formula: $-R_{33}-N(R_{31})_2$, $R_{33}$ representing a $-CH_2-CH_2-$, $-CH_2-CH_2-CH_2-$ or $-CH_2-CH(CH_3)-$ group, $R_{31}$ having the meanings mentioned above, and also the higher homologues of these radicals and containing up to 6 carbon atoms, r is such that the molecular weight is from 500 to 6,000,000, such as from 1,000 to 1,000,000.

(8) amphoteric polymers of the type -D-X-D-X— chosen from:

a) polymers obtained by the action of chloroacetic acid or sodium chloroacetate on compounds containing at least one unit of formula:

$$-D-X-D-X-D-\quad\quad(XXI)$$

where D denotes a radical

and X denotes the symbol E or E', E or E', which may be identical or different, denote a divalent radical which is an alkylene radical with a straight or branched chain comprising up to 7 carbon atoms in the main chain, which is unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups;

b) polymers of formula:

$$-D-X-D-X-\quad\quad(XXII)$$

where D denotes a radical

and X denotes the symbol E or E' and at least one E'; E having the meaning given above and E' being a divalent radical which is an alkylene radical with a straight or branched chain comprising up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily comprising one or more carboxyl functions or one or more hydroxyl functions and betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also comprise other vinyl comonomers such as vinylcaprolactam.

Representative amphoteric polymers that can be used according to the invention are those of (1).

According to the invention, the amphoteric polymer(s) may represent from 0.01% to 10% by weight relative to the total weight of the composition, such as from 0.05% to 5% by weight and further such as from 0.1% to 3% by weight relative to the total weight of the composition.

The ready-to-use composition according to the invention can further comprises one or more additional surfactants in the dye composition (A) and/or in the oxidizing composition (B).

The additional surfactant(s) may be chosen, without discrimination, alone or as mixtures, from anionic, amphoteric, nonionic, zwitterionic, and cationic surfactants.

The additional surfactants that are suitable for carrying out the present invention may be the following, for example:

(i) Anionic Surfactant(s):

By way of example of anionic surfactants which can be used, alone or as mixtures, in the context of the present invention, mention may be made (nonlimiting list) of salts (for example, alkali metal salts, such as sodium salts, ammonium salts, amine salts, amino alcohol salts, or magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, α-olefin sulphonates, paraffin sulphonates; ($C_6$-$C_{24}$) alkyl sulphosuccinates, ($C_6$-$C_{24}$)alkyl ether sulphosuccinates, ($C_6$-$C_{24}$)alkylamide sulphosuccinates; ($C_6$-$C_{24}$)alkyl sulphoacetates; ($C_6$-$C_{24}$)acyl sarcosinates; and ($C_6$-$C_{24}$)acyl glutamates. It is also possible to use ($C_6$-$C_{24}$)alkylpolyglycoside carboxylic esters such as alkylglucoside citrates, alkylpolyglycoside tartrates and alkylpolyglycoside sulphosuccinates, alkylsulphosuccinamates; acyl isethionates and N-acyl taurates, the alkyl or acyl radical of all of these different compounds can comprise from 12 to 20 carbon atoms and the aryl radical may denote a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; acyl lactylates in which the acyl radical comprise from 8 to 20 carbon atoms. It is also possible to use alkyl D-galactoside uronic acids and their salts, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and their salts, such as those comprising from 2 to 50 alkylene oxide groups, for example ethylene oxide groups, and mixtures thereof.

(ii) Nonionic Surfactant(s):

The nonionic surfactants are, themselves also, compounds that are well known by one of ordinary skill in the art (see, for example, "Handbook of Surfactants" by M. R. Porter, published by Blackle & Son (Glasgow and London), 1991, pp. 116-178) and their nature is not a critical factor in the context of the present invention. Thus, they can be chosen from (nonlimiting list) polyethoxylated or polypropoxylated, alkylphenols, alpha-diols or alcohols, comprising a fatty chain that comprises, for example, 8 to 18 carbon atoms, wherein the number of ethylene oxide or propylene oxide groups can range from 2 to 50, for example. Mention may also be made of copolymers of ethylene oxide and of propylene oxide, condensates of ethylene oxide and of propylene oxide with fatty alcohols; polyethoxylated fatty amides comprising from 2 to 30 mol of ethylene oxide, polyglycerolated fatty amides comprising on average 1 to 5 glycerol groups, such as from 1.5 to 4 glycerol groups; polyethoxylated fatty amines comprising from 2 to 30 mol of ethylene oxide; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$-$C_{14}$)alkylamine oxides or N-acylaminopropylmorpholine oxides. It will be noted that alkylpolyglycosides are nonionic surfactants that can be used within the context of the present invention, as are ethoxylated fatty alcohols.

(iii) Amphoteric or Zwitterionic Surfactant(s):

The amphoteric or zwitterionic surfactants, the nature of which is not a critical factor in the context of the present invention, can be, for example (nonlimiting list), aliphatic secondary or tertiary amine derivatives in which the aliphatic radical is a linear or branched chain comprising 8 to 18 carbon atoms and containing at least one water-solubilizing anionic group (for example carboxylate, sulphonate, sulphate, phosphate or phosphonate); mention may also be made of ($C_8$-$C_{20}$)alkylbetaines, sulphobetaines, ($C_8$-$C_{20}$)alkylamido($C_1$-$C_6$)alkylbetaines or ($C_8$-$C_{20}$)alkylamido($C_1$-$C_6$) alkylsulphobetaines.

Among the amine derivatives, mention may be made of the products sold under the name Miranol, as described in U.S. Pat. Nos. 2,528,378 and 2,781,354 and classified in the CTFA dictionary, 3rd edition, 1982 (the disclosures of which are incorporated herein by reference, under the names Amphocarboxyglycinates and Amphocarboxypropionates, with the respective structures:

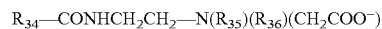

in which: $R_{34}$ denotes an alkyl radical of an acid $R_{34}$—COOH present in hydrolysed coconut oil, a heptyl, nonyl or undecyl radical, $R_{35}$ denotes a beta-hydroxyethyl group and $R_{36}$ denotes a carboxymethyl group; and

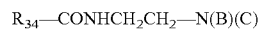

in which:
B represents —$CH_2CH_2OX'$, C represents —$(CH_2)_z$—Y', with z=1 or 2,
X' denotes the —$CH_2CH_2$—COOH group or a hydrogen atom,
Y' denotes —COOH or the —$CH_2$—CHOH—$SO_3H$ radical,
$R_{34'}$ denotes an alkyl radical of an acid $R_{37}$—COOH present in coconut oil or in hydrolysed linseed oil, an alkyl radical, such as a $C_7$, $C_9$, $C_{11}$ or $C_{13}$ alkyl radical, a $C_{17}$ alkyl radical and its isoform, or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphopropionate, Disodium Caprylamphodipropionate, Disodium Caprylamphodipropionate, Lauroamphodipropionic acid and Cocoamphodipropionic acid.

By way of example, mention may be made of the cocoamphodiacetate sold under the trade name Miranol® C2M concentrate by the company Rhodia Chimie.

(iv) Cationic Surfactants:

Among the cationic surfactants, mention may be made, for example, (non-limiting list) of: salts of optionally polyoxyalkylenated primary, secondary, or tertiary fatty amines; quaternary ammonium salts such as tetraalkylammonium, alkylamidoalkyltrialkylammonium, trialkylbenzylammonium, trialkylhydroxyalkylammonium or alkylpyridinium chlorides or bromides; imidazoline derivatives; or amine oxides of cationic nature.

The amounts of the additional surfactants present in the composition according to the invention can range from 0.01% to 40% such as from 0.1% to 30% relative to the total weight of the composition.

The ready-to-use composition according to the invention can also contain in the dye composition (A) and/or the oxidizing composition (B) agents for adjusting the rheology, such as cellulosic thickeners (hydroxyethylcellulose, hydroxypropylcellulose, carboxymethylcellulose, etc.), guar gum and its derivatives (hydroxypropyl guar, etc.), gums of microbial origin (xanthan gum, scleroglucan gum, etc.), synthetic thickeners not comprising a fatty chain, such as crosslinked homopolymers of acrylic acid or of acrylamidopropanesulphonic acid and synthetic thickeners comprising at least one fatty chain.

The thickening polymers comprising at least one fatty chain are of nonionic, anionic, or amphoteric type.

Among the thickening polymers comprising at least one fatty chain and of anionic type, mention may be made of:

(I) those comprising at least one hydrophilic unit and at least one fatty-chain allyl ether unit, such as those in which the hydrophilic unit comprises of an ethylenic unsaturated anionic monomer, for example a vinylcarboxylic acid, an acrylic acid, a methacrylic acid, or mixtures thereof, and in which the fatty-chain allyl ether unit corresponds to the monomer of formula (XXIII) below:

$$CH_2=CR'CH_2OB_nR \qquad (XXIII)$$

in which R' denotes H or $CH_3$, B denotes an ethyleneoxy radical, n is zero or denotes an integer ranging from 1 to 100, R denotes a hydrocarbon-based radical chosen from alkyl, arylalkyl, aryl, alkylaryl, and cycloalkyl radicals, comprising from 8 to 30 carbon atoms, such as from 10 to 24 carbon atoms and further such as from 12 to 18 carbon atoms. A unit of formula (XXIII) which can be used is a unit in which R' denotes H, n is equal to 10 and R denotes a stearyl ($C_{18}$) radical.

Anionic amphiphilic polymers of this type are described and prepared, according to an emulsion polymerization process, in patent EP-0 216 479 (the disclosure of which is incorporated herein by reference), for example.

Representative fatty-chain anionic thickening polymers which can be used according to the invention are polymers formed from 20% to 60% by weight of acrylic acid and/or of methacrylic acid, from 5% to 60% by weight of lower alkyl (meth)acrylates, from 2% to 50% by weight of fatty-chain allyl ether of formula (XXIII), and from 0% to 1% by weight of a crosslinking agent which is a well-known copolymerizable unsaturated polyethylenic monomer, for instance diallyl phthalate, allyl(meth)acrylate, divinylbenzene, (poly)ethylene glycol dimethacrylate, or methylenebisacrylamide.

Among the latter polymers, representative examples such as crosslinked terpolymers of methacrylic acid, of ethyl acrylate and of polyethylene glycol (10 EO) stearyl ether (Steareth-10), for example those sold by the company Allied Colloids under the names Salcare SC 80 and Salcare SC 90, which are aqueous 30% emulsions of a crosslinked terpolymer of methacrylic acid, of ethyl acrylate and of steareth-10 allyl ether (40/50/10).

(II) those comprising at least one hydrophilic unit of unsaturated olefinic carboxylic acid type, and at least one hydrophobic unit of ($C_{10}$-$C_{30}$)alkyl ester of unsaturated carboxylic acid type.

For instance, these polymers can be chosen from those in which the hydrophilic unit of unsaturated olefinic carboxylic acid type corresponds to the monomer of formula (XXIV) below:

(XXIV)

in which $R_1$ denotes H or $CH_3$ or $C_2H_5$, such as acrylic acid, methacrylic acid, or ethacrylic acid units, and of which the hydrophobic unit of ($C_{10}$-$C_{30}$)alkyl ester of unsaturated carboxylic acid type corresponds to the monomer of formula (XXV) below:

(XXV)

in which $R_2$ denotes H or $CH_3$ or $C_2H_5$, for example like acrylate, methacrylate, or ethacrylate units, such as methacrylate and acrylate units, and $R_3$ denoting a $C_{10}$-$C_{30}$ alkyl such as a $C_{12}$-$C_{22}$ alkyl radical.

($C_{10}$-$C_{30}$) alkyl esters of unsaturated carboxylic acids in accordance with the invention include, for example, lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate, and dodecyl methacrylate.

Anionic polymers of this type are described and prepared, for example, according to U.S. Pat. Nos. 3,915,921 and 4,509,949 (the disclosures of which are incorporated herein by reference).

Among the fatty-chain anionic thickening polymers of this type which can be used are polymers formed from a monomer blend comprising:

(i) acrylic acid,
(ii) an ester of formula (XXV) described above in which $R_2$ denotes H or $CH_3$, $R_3$ denoting an alkyl radical comprising from 12 to 22 carbon atoms,
(iii) and a crosslinking agent, which can be a well-known copolymerizable polyethylenic unsaturated monomer, for instance diallyl phthalate, allyl(meth)acrylate, divinylbenzene, (poly)ethylene glycol dimethacrylate, and methylenebisacrylamide.

Among fatty-chain anionic thickening polymers of this type which can be used are those comprise of from 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or alternatively those comprise of from 98% to 96% by weight of acrylic acid (hydrophilic unit), 1% to 4% by weight of $C_{10}$-$C_{30}$ alkyl acrylate (hydrophobic unit) and 0.1% to 0.6% by weight of crosslinking polymerizable monomer such as those described above.

Among the said above polymers, those which can be used according to the present invention are the products sold by the company Goodrich under the trade names Pemulen TR1, Pemulen TR2 and Carbopol 1382, and further examples include Pemulen TR1, and the product sold by the company S.E.P.P.I.C under the name Coatex SX.

(III) maleic anhydride/C30-$C_{38}$ α-olefin/alkyl maleate terpolymers, such as the product (maleic anhydride/$C_{30}$-$C_{38}$ α-olefin/isopropyl maleate copolymer) sold under the name Performa V 1608 by the company Newphase Technologies.

(IV) acrylic terpolymers comprising:
(a) about 20% to 70% by weight of a carboxylic acid comprising α,β-monoethylenic unsaturation,
(b) about 20% to 80% by weight of a non-surfactant monomer comprising α,β-monoethylenic unsaturation other than (a),
(c) about 0.5% to 60% by weight of a nonionic monourethane which is the product of reaction of a monohydric surfactant with a monoisocyanate comprising monoethylenic unsaturation, such as those described in patent application EP-A-0 173 109 (the disclosure of which is incorporated herein by reference) such as the terpolymer described in Example 3, namely a methacrylic acid/methyl acrylate/behenyl dimethyl-meta-isopropenylbenzyl isocyanate ethoxylated (40 EO) terpolymer, as an aqueous 25% dispersion.

(V) copolymers comprising among their monomers a carboxylic acid comprising α,β-monoethylenic unsaturation and an ester of a carboxylic acid containing α,β-monoethylenic unsaturation and of an oxyalkylenated fatty alcohol.

For example, these compounds can further comprise as monomer an ester of a carboxylic acid comprising α,β-monoethylenic unsaturation and of a $C_1$-$C_4$ alcohol.

An example of a compound of this type which may be mentioned is Aculyn 22 sold by the company Rohm & Haas, which is a methacrylic acid/ethyl acrylate/stearyl methacrylate oxyalkylenated terpolymer.

The fatty-chain thickening polymers of nonionic type which can be used according to the invention can be chosen from:

(1) celluloses modified with groups comprising at least one fatty chain; examples which may be mentioned include:
hydroxyethylcelluloses modified with groups comprising at least one fatty chain, such as alkyl, arylalkyl, or alkylaryl groups, or mixtures thereof, and in which the alkyl groups can be $C_8$-$C_{22}$, for instance the product Natrosol Plus Grade 330 CS ($C_{16}$ alkyls) sold by the company Aqualon, or the product Bermocoll EHM 100 sold by the company Berol Nobel,
those modified with alkylphenyl polyalkylene glycol ether groups, such as the product Amercell Polymer HM-1 500 (nonylphenyl polyethylene glycol (15) ether) sold by the company Amerchol.

(2) hydroxypropylguars modified with groups comprising at least one fatty chain, such as the product Esaflor HM 22 ($C_{22}$ alkyl chain) sold by the company Lamberti, and the products RE210-18 ($C_{14}$ alkyl chain) and RE205-1 ($C_{20}$ alkyl chain) sold by the company Rhône-Poulenc.

(3) copolymers of vinylpyrrolidone and of fatty-chain hydrophobic monomers; examples which may be mentioned include:
the products Antaron V216 or Ganex V216 (vinylpyrrolidone/hexadecene copolymer) sold by the company I.S.P.
the products Antaron V220 or Ganex V220 (vinylpyrrolidone/eicosene copolymer) sold by the company I.S.P.

(4) copolymers of $C_1$-$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208.

(5) copolymers of hydrophilic methacrylates or acrylates and of hydrophobic monomers comprising at least one fatty chain, such as, for example, the polyethylene glycol methacrylate/lauryl methacrylate copolymer.

(6) polyether polyurethanes comprising in their chain both hydrophilic blocks usually of polyoxyethylenated nature and hydrophobic blocks which may be aliphatic sequences alone and/or cycloaliphatic and/or aromatic sequences.

(7) polymers with an aminoplast ether skeleton comprising at least one fatty chain, such as the Pure Thix compounds sold by the company Sud-Chemie.

For example, the polyether polyurethanes comprise at least two hydrocarbon-based lipophilic chains comprising from 6 to 30 carbon atoms, separated by a hydrophilic block, the hydrocarbon-based chains possibly being pendent chains, or chains at the end of the hydrophilic block. For example, it is possible for one or more pendent chains to be included. In addition, the polymer may further comprise a triblock copolymer whose hydrophilic block is a polyoxyethylenated hydrocarbon-based chain at one end or at both ends of a hydrophilic block.

The polyether polyurethanes may be multiblock, for example in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyether polyurethanes may comprise from 50 to 1000 oxyethylene groups. The nonionic polyether polyurethanes can comprise a urethane linkage between the hydrophilic blocks, whence arises the name.

By extension, also included among the nonionic fatty-chain polyether polyurethanes are those in which the hydrophilic blocks are linked to the lipophilic blocks via other chemical bonds.

As examples of nonionic fatty-chain polyether polyurethanes which may be used in the invention, use may also be made of Rheolate 205 comprising a urea function, sold by the company Rheox, or Rheolate 208, 204 or 212, and also Acrysol RM 184, Aculyn 44 and Aculyn 46 from the company Rohm & Haas [Aculyn 46 is a polycondensate of polyethylene glycol comprising 150 or 180 mol of ethylene oxide, of stearyl alcohol, and of methylenebis(4-cyclohexyl isocyanate) (SMDI), at 15% by weight in a matrix of maltodextrin (4%) and water (81%); Aculyn 44 is a polycondensate of polyethylene glycol comprising 150 or 180 mol of ethylene oxide, of decyl alcohol and of methylenebis(4-cyclohexyl isocyanate) (SMDI), at 35% by weight in a mixture of propylene glycol (39%) and water (26%)].

Mention may also be made of the product Elfacos T210 comprising a $C_{12-14}$ alkyl chain, and the product Elfacos T212 comprising a $C_{18}$ alkyl chain, from Akzo.

The product DW 1206B from Rohm & Haas comprising a $C_{20}$ alkyl chain and urethane linkage, sold at a solids content of 20% in water, may also be used.

It is also possible to use solutions or dispersions of these polymers, especially in water or in aqueous-alcoholic medium. Examples of such polymers which may be mentioned are Rheolate 255, Rheolate 278 and Rheolate 244 sold by the company Rheox. The products DW 1206F and DW 1206J sold by the company Rohm & Haas may also be used.

The polyether polyurethanes which may be used according to the invention are described, for example, in the article by G. Fonnum, J. Bakke and F k. Hansen, Colloid Polym. Sci 271, 380-389 (1993), the disclosures of which is incorporated herein by reference.

The fatty-chain thickening polymers of amphoteric type used in the present invention comprise at least one fatty chain comprise from 8 to 30 carbon atoms, and may be chosen, for example, from polymers derived from polyaspartic acid comprising at least one fatty chain comprise from 8 to 30 carbon atoms, such as those described and prepared in patent application EP 0 767 191 (the disclosure of which is incorporated herein by reference). Such polymers can be prepared, in a known manner, by reacting polysuccinimide (PSI) with fatty-chain ($C_8$-$C_{24}$) amines, in a solvent medium, in the presence or absence of a basic catalyst such as, for example, aliphatic tertiary amines, followed by amphoterization of the product obtained by reacting with a haloorganic acid.

Among the $C_8$-$C_{24}$ fatty-chain amines that are reacted with PSI, mention may be made of octylamine, nonylamine, decylamine, dodecylamine, tetradecylamine, hexadecylamine, octadecylamine, octadecenylamine, eicosyldecylamine, octynylamine, decenylamine, dodecenylamine, tetradecenylamine, hexadecenylamine, octadecenylamine, and eicosenylamine.

Examples of such polymers are prepared by reacting PSI with n-laurylamine or n-stearylamine in the presence of N,N-dimethyl-1,3-propanediamine as basic catalyst, followed by amphoterization of the product obtained by reaction with potassium monochloroacetate. These polymers are prepared with further details on pages 13 to 20 (lines 1-4) and in Examples 1 to 5 on pages 28 to 34 (lines 1-4) of patent application EP-0 767 191, the disclosure of which is incorporated herein by reference, and such as those described and prepared in patent application EP-0 884 344, the disclosure of which is incorporated herein by reference. Such polymers are prepared by reacting ammonia gas with a $C_8$-$C_{24}$ alkyl or alkenyl monomaleate, in a solvent medium, under reduced pressure and at a temperature of 120-140° C. for 4 to 6 hours.

The $C_8$-$C_{24}$ alkyl or alkenyl radicals may be chosen from the following linear or branched radicals: decyl, dodecyl, tetradecyl, hexadecyl, octadecyl, and oleyl.

Examples of such polymers which comprise aspartic acid units and decyl aspartate units, polymers comprising aspartic acid units and dodecyl aspartate units, polymers comprising aspartic acid units and cetyl aspartate units, polymers comprising aspartic acid units and stearyl aspartate units, and polymers comprising aspartic acid units and n-decylaspartamide units, as described, for instance, in Examples 1 to 6 of the patent application EP-0 959 094, the disclosure of which is incorporated herein by reference. Such polymers are prepared by reacting, in a solvent medium, ammonia gas with a hydrophobic maleic acid monoamide, polyoxyalkylenated and modified with a linear or branched $C_8$-$C_{30}$ alkyl or alkenyl chain, optionally as a mixture with a maleic acid monoester.

An example of a polymer that can be prepared is described, for instance, in Example 2, page 11 of the patent application EP-0 959 090, the disclosure of which is incorporated herein by reference. Such hydrophobic modified polymers of high molecular weight are obtained from maleic acid derivatives and ammonia gas and di- or polyfunctional alcohols or amines, for instance.

Examples of copolymers comprising aspartic acid and cetyl aspartate units or comprising aspartic acid and cetyl aspartate units are mentioned, respectively, in Examples 3 and 5 of patent application EP-0 959 091 (the disclosure of which is incorporated herein by reference), for example. Such hydrophobic modified polymers can be prepared from maleic acid monoester or monoamide and ammonia gas, for instance.

Examples of such polymers are given in Examples 1, 2, 3 and 5 of the said patent application, for instance.

For example, the amphoteric polymers used in the instant invention can comprise at least one fatty chain comprising from 8 to 30 carbon atoms can be chosen from those comprising at least one non-cyclic cationic unit. The ones that can be used are those prepared from or comprising 1 to 20 mol % of monomer comprising a fatty chain, such as 1.5 to 15 mol % and further such as 1.5 to 6 mol % relative to the total number of moles of monomers.

The said fatty-chain amphoteric polymers according to the invention can comprise, or are prepared by copolymerizing:

1) at least one monomer of formula (Ib) or (Ic):

$$R_1-\underset{H}{C}=\underset{R_2}{C}-\underset{O}{\overset{\|}{C}}-Z-(C_nH_{2n})-\overset{R_3}{\underset{R_4}{\overset{|}{N^+}}}-R_5 \quad A^- \quad \text{(Ib)}$$

$$R_1-\underset{H}{C}=\underset{R_2}{C}-\underset{O}{\overset{\|}{C}}-Z-(C_nH_{2n})-N\overset{R_3}{\underset{R_4}{<}} \quad \text{(Ic)}$$

in which $R_1$ and $R_2$, which may be identical or different, represent a hydrogen atom or a methyl radical, $R_3$, $R_4$ and $R_5$, which may be identical or different, represent a linear or branched alkyl radical comprising from 1 to 30 carbon atoms, Z represents an NH group or an oxygen atom, n is an integer from 2 to 5, $A^-$ is an anion derived from an organic or mineral acid, such as a methosulphate anion or a halide such as chloride or bromide;

2) at least one monomer of formula (IIb)

$$R_6-CH=CR_7-COOH \quad \text{(IIb)}$$

in which $R_6$ and $R_7$, which may be identical or different, represent a hydrogen atom or a methyl radical; and 3) at least one monomer of formula (IIIa):

$$R_6-CH=CR_7-COXR_8 \quad \text{(IIIa)}$$

in which $R_6$ and $R_7$, which may be identical or different, represent a hydrogen atom or a methyl radical, X denotes an oxygen or nitrogen atom and $R_8$ denotes a linear or branched alkyl radical comprising from 1 to 30 carbon atoms;

at least one of the monomers of formula (Ib), (Ic) or (IIIa) comprising at least one fatty chain.

The monomers of formulae (Ib) and (Ic) of the present invention can be chosen from:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide, dimethylaminopropylacrylamide, these monomers optionally being quaternized, for example with a $C_1$-$C_4$ alkyl halide or a $C_1$-$C_4$ dialkyl sulphate.

For example, the monomer of formula (Ib) can be chosen from acrylamidopropyltrimethylammonium chloride and methacrylamidopropyltrimethylammonium chloride.

The monomers of formula (IIb) of the present invention can be chosen from acrylic acid, methacrylic acid, crotonic acid, and 2-methylcrotonic acid. For instance, the monomer of formula (IIb) is acrylic acid.

The monomers of formula (IIIa) of the present invention can be chosen from $C_{12}$-$C_{22}$ alkyl acrylates or methacrylates such as $C_{16}$-$C_{18}$ alkyl acrylates or methacrylates.

The monomers constituting the fatty-chain amphoteric polymers of the invention can be already neutralized and/or quaternized.

The ratio of the number of cationic charges/anionic charges can be equal to about 1.

The fatty-chain amphoteric polymers according to the invention can comprise from 1 mol % to 10 mol % of the monomer comprising a fatty chain (monomer of formula (Ib), (Ic) or (IIIa)), such as from 1.5 mol % to 6 mol %.

The weight-average molecular weights of the fatty-chain amphoteric polymers according to the invention may range from 500 to 50 000 000 such as from 10 000 and 5 000 000.

The fatty-chain amphoteric polymers according to the invention may also comprise other monomers such as non-ionic monomers and further such as $C_1$-$C_4$ alkyl acrylates or methacrylates.

Fatty-chain amphoteric polymers according to the invention are described and prepared, for example, in patent application WO 98/44012, the disclosure of which is incorporated herein by reference.

Among the fatty-chain amphoteric polymers according to the invention, the ones that are acrylic acid/(meth)acrylamidopropyltrimethylammonium chloride/stearyl methacrylate terpolymers.

In an embodiment of the invention, a fatty-chain thickening polymer of nonionic type can be used in the oxidation dye composition according to the invention.

The thickening polymers can be used in an amount that can range from about 0.01% to about 10% by weight relative to the total weight of the dye composition. For instance, this amount ranges from about 0.1% to about 5% by weight.

The medium for the composition that is suitable for dyeing can be an aqueous medium comprising of water and can further comprise cosmetically acceptable organic solvents other than the polyol(s) of the invention including, for example, other polyols, for instance propylene glycol, alcohols such as ethyl alcohol, isopropyl alcohol, benzyl alcohol and phenylethyl alcohol, or glycol ethers such as, for example, ethylene glycol monomethyl, monoethyl or monobutyl ether, propylene glycol monomethyl ether, and also diethylene glycol alkyl ethers such as, for example, diethylene glycol monoethyl ether or monobutyl ether, in concentrations ranging from about 0.5% to about 20% such as from about 2% to 10% by weight relative to the total weight of the composition.

The composition according to the invention may also comprise an effective amount of other agents, known previously elsewhere in oxidation dyeing, such as various common adjuvants, for instance sequestering agents such as EDTA and etidronic acid, UV screening agents, waxes, volatile or non-volatile, cyclic or linear or branched silicones, which are optionally organomodified (such as with amine groups), preserving agents, ceramides, pseudoceramides, plant, mineral or synthetic oils, vitamins or provitamins, for instance panthenol, opacifiers, etc.

The said composition may also comprise reducing agents or antioxidants. These agents may be chosen from sodium sulphite, thioglycolic acid, thiolactic acid, sodium bisulphite, dehydroascorbic acid, hydroquinone, 2-methylhydroquinone, tert-butylhydroquinone and homogentisic acid, and, in this case, they can be present in amounts ranging from about 0.05% to 3% by weight relative to the total weight of the composition, for instance.

The composition according to the invention can further comprise one or more fatty alcohols, these fatty alcohols being introduced in pure form or as a mixture. Among these, mention may be made of lauryl alcohol, cetyl alcohol, stearyl alcohol, oleyl alcohol, and mixtures thereof. These additional fatty alcohols can represent from 0.001% to 20% by weight approximately relative to the total weight of the composition.

Needless to say, a person skilled in the art will take care to select the optional additional compound(s) mentioned above such that the advantageous properties intrinsically associated with the ready-to-use composition according to the invention are not, or are not substantially, adversely affected by the envisaged addition(s).

In the oxidizing composition (B), the oxidizing agent can be chosen from hydrogen peroxide, urea peroxide, alkali metal bromates or ferricyanides, and persalts such as perborates and persulphates. For example, hydrogen peroxide can be used. This oxidizing agent may comprise of an aqueous hydrogen peroxide solution whose titre may range from about 1 to 40 volumes such as from about 5 to 40 volumes.

Oxidizing agents which may also be used are one or more redox enzymes such as laccases, peroxidases, and 2-electron oxidoreductases (such as uricase), where appropriate in the presence of their respective donor or co-factor.

The pH of the dye composition (A) or of the ready-to-use composition applied to the keratin fibers [composition resulting from mixing together the dye composition (A) and the oxidizing composition (B)] is generally, for example, from 4 to 12. It can range from 6 to 11 and may be adjusted to the desired value using acidifying or basifying agents that are well known in the prior art in the dyeing of keratin fibers.

Among the basifying agents which may be mentioned, for example, are aqueous ammonia, alkali metal carbonates, alkanolamines such as monoethanolamine, diethanolamine and triethanolamine and derivatives thereof, oxyethylenaated and/or oxypropylenated hydroxyalkylamines and ethylenediamines, sodium hydroxide, potassium hydroxide and the compounds of formula (XXVI) below:

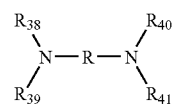

(XXVI)

in which R is a propylene residue optionally substituted with a hydroxyl group or a $C_1$-$C_4$ alkyl radical; $R_{38}$, $R_{39}$, $R_{40}$ and $R_{41}$, which may be identical or different, represent a hydrogen atom, a $C_1$-$C_4$ alkyl radical, or a $C_1$-$C_4$ hydroxyalkyl radical.

The acidifying agents can be, for example, mineral or organic acids, for instance hydrochloric acid, orthophosphoric acid, carboxylic acids, for instance tartaric acid, citric acid, lactic acid, or sulphonic acids.

The dyeing process according to the invention can comprise in applying the ready-to-use composition, prepared extemporaneously at the time of use from compositions (A) and (B) described above, to wet or dry keratin fibers, and in leaving the composition to act for an exposure time, such as ranging from 1 to 60 minutes approximately, and further such as from 10 to 45 minutes approximately, in rinsing the fibers and then in optionally washing them with shampoo, rinsing them again and then drying them.

Concrete examples illustrating the invention are given below without, however, being limiting in nature.

EXAMPLES

Example 1

The following composition was prepared:

Dye Composition:

(Expressed in Grams)

| | |
|---|---|
| Oleyl alcohol | 6 |
| Oleic acid | 3 |
| Oleyl alcohol polyglycerolated with 2 mol of glycerol | 6 |
| Oleyl alcohol polyglycerolated with 6 mol of glycerol | 6 |
| Diethylaminopropyl laurylaminosuccinamate, sodium salt | 3 |
| Oleylamine oxyethylenated with 2 mol of ethylene oxide | 7 |
| Alkyl ether carboxylic acid monoethanolamide comprising 2 mol of ethylene oxide | 10 |
| Ammonium acetate | 0.8 |
| Hexylene glycol | 20 |
| Reducing agents, antioxidants | 0.915 |
| Sequestering agent | 1 |
| 1,3-Dihydroxybenzene (resorcinol) | 0.085 |
| para-Phenylenediamine | 0.27 |
| 5-N-(β-Hydroxyethyl)amino-2-methylphenol | 0.16 |
| 2-Methyl-5-aminophenol | 1.12 |
| para-Aminophenol | 0.2 |
| 6-Hydroxyindole | 0.045 |
| Fragrance | qs |
| Aqueous ammonia (containing 20.5% ammonia) | 10.2 |
| Demineralized water qs | 100 |

The dye composition was mixed, at the time of use, in a plastic bowl and for 2 minutes, with an oxidizing composition having a titre of 20 volumes of aqueous hydrogen peroxide solution, at a rate of 1 part of dye composition per 1 part of oxidizing composition.

The mixture obtained was applied to locks of hair containing 90% grey hairs, and was left in place for 30 minutes.

The locks were then rinsed with water, washed with shampoo, rinsed again with water and then dried and disentangled.

A particularly strong dark red-blond shade was then obtained on hair sensitized with a permanent wave.

Example 2

The following composition was prepared:

Dye Composition:

(Expressed in Grams)

| | |
|---|---|
| Oleyl alcohol | 4 |
| Oleic acid | 5 |
| Oleyl alcohol polyglycerolated with 2 mol of glycerol | 4 |
| Lauryl alcohol polyglycerolated with 4 mol of glycerol | 3.6 |
| Rapeseed acid amide oxyethylenated with 4 mol of ethylene oxide | 7.99 |
| Oleylamine oxyethylenated with 2 mol of ethylene oxide | 4 |
| Decyl alcohol oxyethylenated with 3 mol of ethylene oxide | 2.7 |
| Ethyl alcohol | 7.45 |
| 3-Methyl-1,5-pentanediol | 15 |
| Reducing agents, antioxidants | 0.63 |
| Sequestering agent | 1 |
| 1,3-Dihydroxybenzene (resorcinol) | 0.49 |
| para-Phenylenediamine | 0.50 |
| 1,3-Dihydroxy-2-methylbenzene | 0.17 |
| 3-Methyl-1-phenyl-5-pyrazolone | 0.15 |
| 2,4-Diamino-1-(β-hydroxyethyloxy)benzene dihydrochloride | 0.049 |
| Pure monoethanolamine | 2 |
| Fragrance | qs |
| Aqueous ammonia (containing 20.5% ammonia) | 10 |
| Demineralized water qs | 100 |

The dye composition was mixed, at the time of use, in a plastic bowl and for 2 minutes, with an oxidizing composition having a titre of 20 volumes of aqueous hydrogen peroxide solution, at a rate of 1 part of dye composition per 1 part of oxidizing composition.

The mixture obtained was applied to locks of hair containing 90% grey hairs, and was left in place for 30 minutes.

The locks were then rinsed with water, washed with shampoo, rinsed again with water and then dried and disentangled.

A light chestnut shade was then obtained.

Example 3

The following composition was prepared:

Dye Composition:

(Expressed in Grams)

| | |
|---|---|
| Oleic acid | 3 |
| Oleyl alcohol polyglycerolated with 4 mol of glycerol | 5.46 |
| Lauryl alcohol polyglycerolated with 1.5 mol of glycerol | 5 |
| Alkyl(70/30 C13/C15 - 50% linear) ether carboxylic acid monoethanolamide oxyethylenated with 2 mol of ethylene oxide | 5 |
| Decyl alcohol oxyethylenated with 5 mol of ethylene oxide | 5.4 |
| Ethyl alcohol | 6.52 |
| 2,2-Dimethyl-1,3-propanediol (neopentyl glycol) | 12 |
| Reducing agents, antioxidants | 0.774 |
| Sequestering agent | 1.2 |
| 6-Hydroxybenzomorpholine | 3.018 |
| para-Phenylenediamine | 2.39 |
| 1,3-Dihydroxy-2-methylbenzene | 0.165 |
| 3-Methyl-1-phenyl-5-pyrazolone | 0.15 |
| 2,4-Diamino-1-(β-hydroxyethyloxy)benzene dihydrochloride | 0.196 |
| Pure monoethanolamine | 2 |
| Fragrance | qs |
| Aqueous ammonia (containing 20.5% ammonia) | 12 |
| Demineralized water qs | 100 |

The dye composition was mixed, at the time of use, in a plastic bowl and for 2 minutes, with an oxidizing composition having a titre of 20 volumes of aqueous hydrogen peroxide solution, at a rate of 1 part of dye composition per 1 part of oxidizing composition.

The mixture obtained was applied to locks of hair containing 90% grey hairs, and was left in place for 30 minutes.

The locks were then rinsed with water, washed with shampoo, rinsed again with water and then dried and disentangled.

A black shade was then obtained.

What is claimed is:

1. A composition for the oxidation dyeing of a keratin fibre comprising, in a medium that is suitable for dyeing,
    at least one oxidation dye,
    at least one fatty alcohol chosen from mono- and polyglycerolated fatty alcohols, and
    at least one polyol chosen from 3-methyl-1,3,5-pentanetriol, 1,2,4-butanetriol, 1,5-pentanediol, 2-methyl-1,3-propanediol, 3-methyl-1,5-pentanediol, neopentyl glycol, isoprene glycol, and hexylene glycol; and
wherein the composition contains no glycerol and no cationic synthetic thickening polymer comprising at least one fatty chain.

2. The composition according to claim 1, wherein the keratin fibre is human keratin fibre.

3. The composition according to claim 2, wherein the human keratin fibre is hair.

4. The composition according to claim 1, wherein said at least one fatty alcohol is chosen from formula (IIa) below:

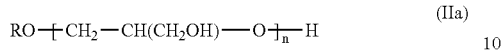

in which:
R is chosen from saturated and unsaturated, linear and branched radicals comprising from 8 to 40 carbon atoms; and
n ranges from 1 to 30.

5. The composition according to claim 4, wherein R of formula (IIa) comprises from 10 to 30 carbon atoms.

6. The composition according to claim 4, wherein n of formula (IIa) ranges from 1 to 10.

7. The composition according to claim 1, wherein said at least one fatty alcohol represents from 0.01% to 30% by weight relative to the total weight of the composition.

8. The composition according to claim 7, wherein said at least one fatty alcohol represents from 0.05% to 20% by weight relative to the total weight of the composition.

9. The composition according to claim 8, wherein said at least one fatty alcohol represents from 0.1% to 15% by weight relative to the total weight of the composition.

10. The composition according to claim 9, wherein said at least one polyol is chosen from hexylene glycol, neopentyl glycol, and 3-methyl-1,5-pentanediol.

11. The composition according to claim 1, wherein said at least one polyol represents from 0.1% to 40% relative to the total weight of the composition.

12. The composition according to claim 11, wherein said at least one polyol represents from 0.5% to 30% relative to the total weight of the composition.

13. The composition according to claim 12, wherein said at least one polyol of formula (Ia) represents from 1% to 20% relative to the total weight of the composition.

14. The composition according to claim 1, wherein said at least one oxidation dye is chosen from oxidation bases and couplers.

15. The composition according to claim 14, wherein the composition comprises at least one oxidation base.

16. The composition according to claim 15, wherein said at least one oxidation base is chosen from ortho- and para-phenylenediamines, double bases, ortho- and para-aminophenols, heterocyclic bases, and the addition salts thereof with an acid.

17. The composition according to claim 16, wherein the para-phenylenediamines are chosen from compounds of formula (II) below:

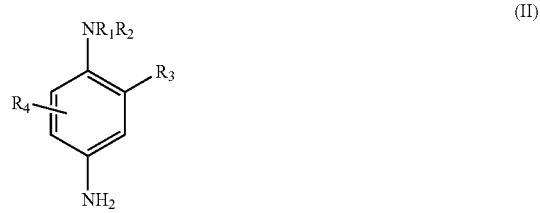

in which:
$R_1$ is chosen from a hydrogen atom, $C_1$-$C_4$ alkyl radicals, $C_1$-$C_4$ monohydroxyalkyl radicals, $C_2$-$C_4$ polyhydroxyalkyl radicals, $(C_1$-$C_4)$alkoxy$(C1$-$C4)$alkyl radicals and $C_1$-$C_4$ alkyl radicals substituted with a group chosen from nitrogenous, phenyl, and 4'-aminophenyl groups;
$R_2$ is chosen from a hydrogen atom, $C_1$-$C_4$ alkyl radicals, $C_1$-$C_4$ monohydroxyalkyl radicals, $C_2$-$C_4$ polyhydroxyalkyl radicals, $(C_1$-$C_4)$alkoxy$(C_1$-$C_4)$alkyl radicals and $C_1$-$C_4$ alkyl radicals substituted with a nitrogenous group;
$R_1$ and $R_2$ optionally form, with the nitrogen atom which bears them, a heterocycle chosen from 5- and 6-membered nitrogenous heterocycles optionally substituted with at least one substituent chosen from alkyl, hydroxyl, and ureido groups;
$R_3$ is chosen from a hydrogen atom, a halogen atom, $C_1$-$C_4$ alkyl radicals, a sulpho radical, a carboxy radical, $C_1$-$C_4$ monohydroxyalkyl radicals, $C_1$-$C_4$ hydroxyalkoxy radicals, acetylamino$(C_1$-$C_4)$alkoxy radicals, mesylamino $(C_1$-$C_4)$alkoxy radicals, and carbamoylamino$(C_1$-$C_4)$ alkoxy radicals; and
$R_4$ is chosen from a hydrogen atom, a halogen atom, and $C_1$-$C_4$ alkyl radicals.

18. The composition according to claim 16, wherein the double bases are chosen from compounds of structure (III) below:

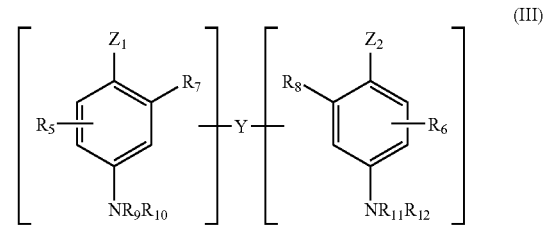

in which:
$Z_1$ and $Z_2$, which may be identical or different, are chosen from a hydroxyl radical and a —$NH_2$ radical which may be substituted with at least one substituent chosen from $C_1$-$C_4$ alkyl radicals and a linker arm Y;
the linker arm Y is chosen from linear and branched alkylene chains comprising from 1 to 14 carbon atoms, which may be interrupted by or terminated with at least one entity chosen from nitrogenous groups and hetero atoms, and optionally substituted with at least one radical chosen from hydroxyl and $C_1$-$C_6$ alkoxy radicals;
$R_5$ and $R_6$ are chosen from a hydrogen atom, a halogen atom, $C_1$-C4 alkyl radicals, $C_1$-$C_4$ monohydroxyalkyl radicals, $C_2$-$C_4$ polyhydroxyalkyl radicals, $C_1$-$C_4$ aminoalkyl radicals, and a linker arm Y;
$R_7$, $R_8$, $R_9$, $R_{10}$, $R_{11}$ and $R_{12}$, which may be identical or different, are chosen from a hydrogen atom, a linker arm Y, and $C_1$-$C_4$ alkyl radicals;
wherein the compounds of formula (III) comprise only one linker arm Y per molecule.

19. The composition according to claim 17, wherein the nitrogenous groups are chosen from amino, mono($C_1$-$C_4$) alkylamino, di($C_1$-$C_4$)alkylamino, tri($C_1$-$C_4$)alkylamino, monohydroxy($C_1$-$C_4$)alkylamino, imidazolinium, and ammonium radicals.

20. The composition according to claim 16, wherein said para-aminophenols are chosen from the compounds of structure (IV) below:

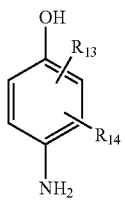

(IV)

in which:
R$_{13}$ is chosen from a hydrogen atom, a halogen atom, and C$_1$-C$_4$ alkyl, C$_1$-C$_4$ monohydroxyalkyl, (C$_1$-C$_4$)alkoxy (C$_1$-C$_4$)alkyl, C$_1$-C$_4$ aminoalkyl, and hydroxy(C$_1$-C$_4$) alkylamino(C$_1$-C$_4$)alkyl radicals, R$_{14}$ is chosen from a hydrogen atom, a halogen atom, and C$_1$-C$_4$ alkyl, C$_1$-C$_4$ monohydroxyalkyl, C$_2$-C$_4$ polyhydroxyalkyl, C$_1$-C$_4$ aminoalkyl, C$_1$-C$_4$ cyanoalkyl, and (C$_1$-C$_4$)alkoxy(C$_1$-C$_4$)alkyl radicals.

21. The composition according to claim 16, wherein the heterocyclic bases are chosen from pyridine derivatives, pyrimidine derivatives, pyrazolopyrimidines, and pyrazole derivatives.

22. The composition according to claim 14, wherein the oxidation bases are present in concentrations ranging from 0.0005% to 12% by weight relative to the total weight of the composition.

23. The composition according to claim 22, wherein the oxidation bases are present in concentrations ranging from 0.005% to 8% by weight relative to the total weight of the composition.

24. The composition according to claim 14, wherein the couplers are chosen from meta-phenylenediamines, meta-aminophenols, meta-diphenols, heterocyclic couplers, and the addition salts thereof with an acid.

25. The composition according to claim 14, wherein the couplers are present in concentrations ranging from 0.0001% to 10% by weight relative to the total weight of the composition.

26. The composition according to claim 25, wherein the couplers are present in concentrations ranging from 0.005% to 5% by weight relative to the total weight of the composition.

27. The composition according to claim 16, wherein the addition salts with an acid of the oxidation bases are chosen from hydrochlorides, hydrobromides, sulphates, tartrates, lactates, and acetates.

28. The composition according to claim 1, wherein the composition further comprises at least one direct dye.

29. The composition according to claim 1, wherein the composition further comprises at least one reducing agent in an amount ranging from 0.05% to 3% by weight relative to the total weight of the composition.

30. The composition according to claim 1, wherein the composition comprises at least one additional fatty alcohol.

31. The composition according to claim 30, wherein said at least one fatty alcohol represents from 0.001% to 20% by weight relative to the total weight of the composition.

32. A ready-to-use composition for the oxidation dyeing of a keratin fibre comprising composition (A) which comprises in a medium that is suitable for dyeing,
at least one oxidation dye,
at least one fatty alcohol chosen from mono- and polyglycerolated fatty alcohols, and at least one polyol chosen from 3-methyl-1,3,5-pentanetriol, 1,2,4-butanetriol, 1,5-pentanediol, 2-methyl-1,3-propanediol, 3-methyl-1,5-pentanediol, neopentyl glycol, isoprene glycol, and hexylene glycol; and wherein the composition contains no glycerol and no cationic synthetic thickening polymer comprising at least one fatty chain and composition (B) which comprises at least one oxidizing agent.

33. The composition according to claim 32, wherein said at least one oxidizing agent is chosen from hydrogen peroxide, urea peroxide, alkali metal bromates, ferricyanides, persalts, redox enzymes, and respective donor or co-factor of said redox enzymes where appropriate.

34. The composition according to claim 33, wherein the at least one oxidizing agent is hydrogen peroxide.

35. The composition according to claim 34, wherein the at least one oxidizing agent is chosen from aqueous hydrogen peroxide solutions with a titre ranging from 1 to 40 volumes.

36. The composition according to claim 1, wherein the composition has a pH ranging from 4 to 12.

37. The composition according to claim 32, wherein at least one of compositions (A) and (B) comprises at least one polymer chosen from cationic and amphoteric polymers.

38. The composition according to claim 37, wherein the cationic polymers are chosen from polyquaternary ammoniums comprising repeating units corresponding to formula (W) below:

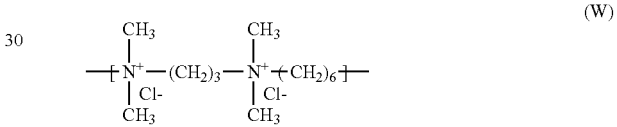

39. The composition according to claim 37, wherein the cationic polymers are chosen from polyquaternary ammoniums comprising repeating units corresponding to formula (U) below:

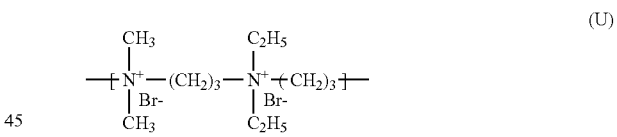

40. The composition according to claim 37, wherein the amphoteric polymers are chosen from copolymers comprising at least one acrylic acid residue and at least one dimethyldiallylammonium salt residue.

41. The composition according to claim 37, wherein said at least one polymer represents from 0.01% to 10% by weight relative to the total weight of the composition.

42. The composition according to claim 41, wherein said at least one polymer represents from 0.05% to 5% by weight relative to the total weight of the composition.

43. The composition according to claim 42, wherein said at least one polymer represents from 0.1% to 3% by weight relative to the total weight of the composition.

44. The composition according to claim 32, wherein at least one of compositions (A) and (B) further comprises at least one additional surfactant chosen from anionic, cationic, nonionic, and amphoteric surfactants.

45. The composition according to claim 44, wherein said at least one additional surfactant represents from 0.01% to 40% of the total weight of the composition.

46. The composition according to claim 45, wherein said at least one additional surfactant represents from 0.1% to 30% of the total weight of the composition.

47. The composition according to claim 32, wherein at least one of compositions (A) and (B) further comprises at least one polymeric thickener chosen from cellulose derivatives, guar derivatives, gums of microbial origin, synthetic thickeners not comprising a fatty chain, and synthetic thickeners, comprising a fatty chain, of nonionic, anionic, or amphoteric nature.

48. The composition according to claim 47, wherein said at least one polymeric thickener is present in a proportion of from 0.01% to 10% by weight relative to the total weight of the composition.

49. The composition according to claim 48, wherein said at least one polymeric thickener is present in a proportion of from 0.1% to 5% by weight relative to the total weight of the composition.

50. A process for dyeing a keratin fibre comprising:
 (i) applying to said fibre a dye composition (A) which comprises in a medium that is suitable for dyeing, at least one oxidation dye,
  at least one fatty alcohol chosen from mono- and polyglycerolated fatty alcohols, and at least one polyol chosen from 3-methyl-1,3,5-pentanetriol, 1,2,4-butanetriol, 1,5-pentanediol, 2-methyl-1,3-propanediol, 3-methyl-1,5-pentanediol, neopentyl glycol, isoprene glycol, and hexylene glycol; and
 wherein the composition contains no glycerol and no cationic synthetic thickening polymer comprising at least one fatty chain;
 (ii) developing colour in alkaline, neutral, or acidic medium with the aid of a composition (B) which comprises at least one oxidizing agent,
 wherein composition (B) is added to composition (A) at the time of use, or is applied sequentially to said keratin fibre without intermediate rinsing.

51. A multi-compartment device or kit for the oxidation dyeing of a keratin fibre wherein said device or kit comprises at least two compartments wherein one compartment comprises composition (A) which comprises in a medium that is suitable for dyeing,
 at least one oxidation dye,
 at least one fatty alcohol chosen from mono- and polyglycerolated fatty alcohols, and at least one polyol chosen from 3-methyl-1,3,5-pentanetriol, 1,2,4-butanetriol, 1,5-pentanediol, 2-methyl-1,3-propanediol, 3-methyl-1,5-pentanediol, neopentyl glycol, isoprene glycol, and hexylene glycol; and
wherein the composition contains no glycerol and no cationic synthetic thickening polymer comprising at least one fatty chain, and wherein the other compartment comprises composition (B) which comprises at least one oxidizing agent.

52. The process according to claim 50, wherein the keratin fibre is human hair.

53. The device or kit according to claim 51, wherein the keratin fibre is human hair.

54. The composition according to claim 24, wherein the addition salts with an acid of the couplers are chosen from hydrochlorides, hydrobromides, sulphates, tartrates, lactates, and acetates.

* * * * *

UNITED STATES PATENT AND TRADEMARK OFFICE
CERTIFICATE OF CORRECTION

PATENT NO.         : 7,402,180 B2
APPLICATION NO. : 11/483637
DATED                 : July 22, 2008
INVENTOR(S)       : Patricia Vuarier et al.

It is certified that error appears in the above-identified patent and that said Letters Patent is hereby corrected as shown below:

In claim 6, column 33, line 20, "1to" should read --1 to--.

In claim 16, column 33, line 50, "ortho-and" should read --ortho- and--.

In claim 17, column 34, line 4, "$(C_1-C_4)$alkoxy(C1-C4)alkyl" should read --$(C_1-C_4)$alkoxy$(C_1-C_4)$alkyl--.

In claim 18, column 34, line 52, "$C_1$-C4" should read --$C_1$-$C_4$--.

In claim 40, column 36, lines 50-51, "dimethyidiallylammonium" should read --dimethyldiallylammonium--.

Signed and Sealed this

Eleventh Day of November, 2008

JON W. DUDAS
*Director of the United States Patent and Trademark Office*